United States Patent [19]
Ghobrial et al.

[11] Patent Number: 6,051,232
[45] Date of Patent: *Apr. 18, 2000

[54] CHIMERIC MHC CLASS I ANTIGENS FOR INDUCING ALLOGRAFT TOLERANCE

[75] Inventors: Rafik R. Ghobrial, Pearland; Stanislaw M. Stepkowski; Barry D. Kahan, both of Houston, all of Tex.

[73] Assignee: Board of Regents, University of Texas System, Austin, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/842,656

[22] Filed: Apr. 15, 1997

Related U.S. Application Data

[63] Continuation of application No. 08/245,337, May 18, 1994, abandoned.

[51] Int. Cl.[7] ...................... A61K 39/385; C07K 14/705; C07K 14/745
[52] U.S. Cl. ................................... 424/192.1; 424/185.1; 424/193.1; 435/69.3; 530/300; 530/350; 530/395; 530/868
[58] Field of Search ..................................... 530/300, 350, 530/395, 868; 424/185.1, 193.1, 192.1; 435/69.3

[56] References Cited

PUBLICATIONS

Jefferies, W. A. et al., EMBO J. 7:3423–31, Cytolytic T cells recognize a chimeric MHC Class I antigen expressed in influenza A infected transgenic mice, 1988.

Paul, W. F. (ed), *Fundamental Immunology*, 4th edition, pp. 1206–1214, Lippincott–Raven, New York, 1999.

Sharabi, Y. et al., J. Exp. Med. 169:493–502, Mixed chimerisim and permanent specific transplantation tolerance induced by a nonlethal preparative regimen, Feb. 1989.

Sykes, M. et al., Transplantation 55:197–202, Specific prolongation of skin graft survival following retroviral transduction of bone marrow with an allogeneic MHC gene, 1993.

Rammensee, H. et al., Immunogenetics 41:178–228, "MHC ligands and peptide motifs: first listing", 1995.

Chueh et al., "Induction of Tolerance Toward Rat Cardiac Allografts by Treatment with Allochimeric Class I MHC Antigen and FTY720[1]", Transplantation, vol. 64, 1407–1414, No. 10, Nov. 27, 1997.

Jatin M. Vyas et al., Department of Microbiology and Immunology and the Department of Medicine, Baylor College of Medicine Houston, TX, Availability of Endogenous Peptides Limits Expression of an $M3^a$—$L^d$ Major Histocompatibility Complex Class I Chimera, J. Exp. Med. The Rockefeller University Press, vol. 179, Jan. 1994, pp. 155–165.

Antonella Vitiello et al, Department of CEllular Immunology, Cytel Corporation, and the Department of Immunology, Scripps Clinic and Research Foundation, La Jolla, CA, "Analysis of the HLA–restricted Influenza–specific Cytotoxic T Lymphocyte Response in Transgenic Mice Carrying a Chimeric Human–Mouse Class I Major Histocompatibility Complex", J. Exp. Med. The Rockefeller University Press, vol. 173, Apr. 1991, pp. 1007–1015.

Bjorkman PJ, Saper MA, Samraoui B, Bennett WS, Stromiger JL, Wiley DC. 1987. Structure of the human class I histocompatibility antigen HLA–A2. *Nature* 1987; 329:506.

Madden DR, Gorga JC, Strominger JL, Wiley DC. The three–dimensional structure of HLA—B27 at 2.1 A resolution suggests a general mechanism for tight peptide binding to MHC. *Cell* 1992; 70:1035.

Silver ML, Guo HC, Strominger JL, Wiley DC. Atomic structure of a human MHC molecule presenting an influenza virus peptide. *Nature* 1992; 360:367.

Young AC, Zhang W. Scchettini JC, Nathenson SG. The three dimensional structure of H2Db at 2.4 A resolution: implications for antigen–determinant selection. *Cell* 1994; 76:39.

Wang M, Stepkowski SM, Wang M, Tian L, Qu X, Tu Y, He G and Kahan BD. Induction of specific allograft immunity by soluble class I MHC heavy chain protein produced in a Baculovirus expression system. *Transplantation* 1996; 61:448.

*Primary Examiner*—Thomas M. Cunningham
*Assistant Examiner*—Martha Lubet
*Attorney, Agent, or Firm*—Fulbright & Jaworski L.L.P.

[57] ABSTRACT

Chimeric MHC Class I molecules having a recipient-type N-terminus, a donor-type alpha-1 helical region, and a recipient-type alpha-2 domain induce tolerance to donor grafts when administered to the recipient at time of transplantation.

19 Claims, 12 Drawing Sheets

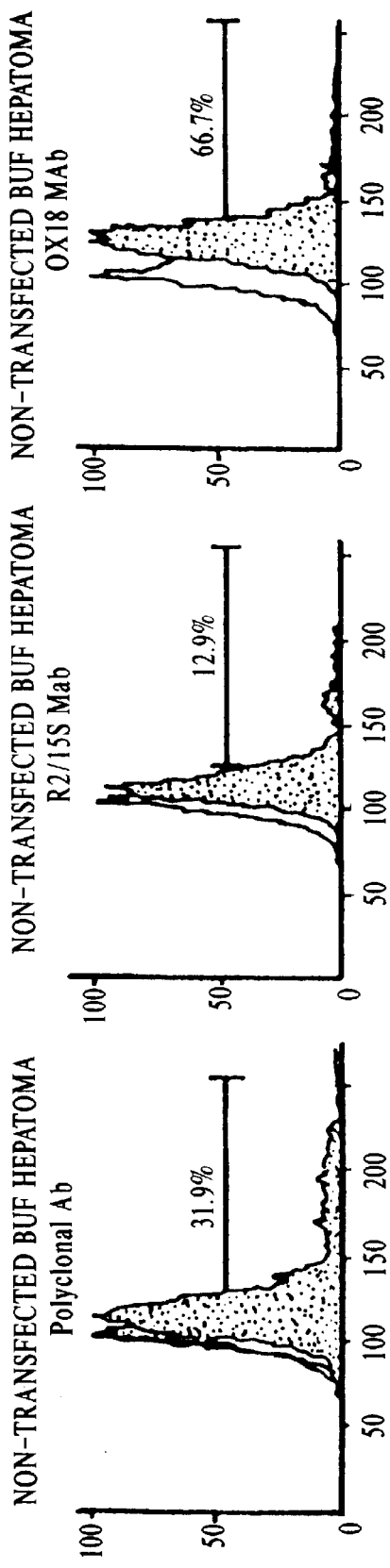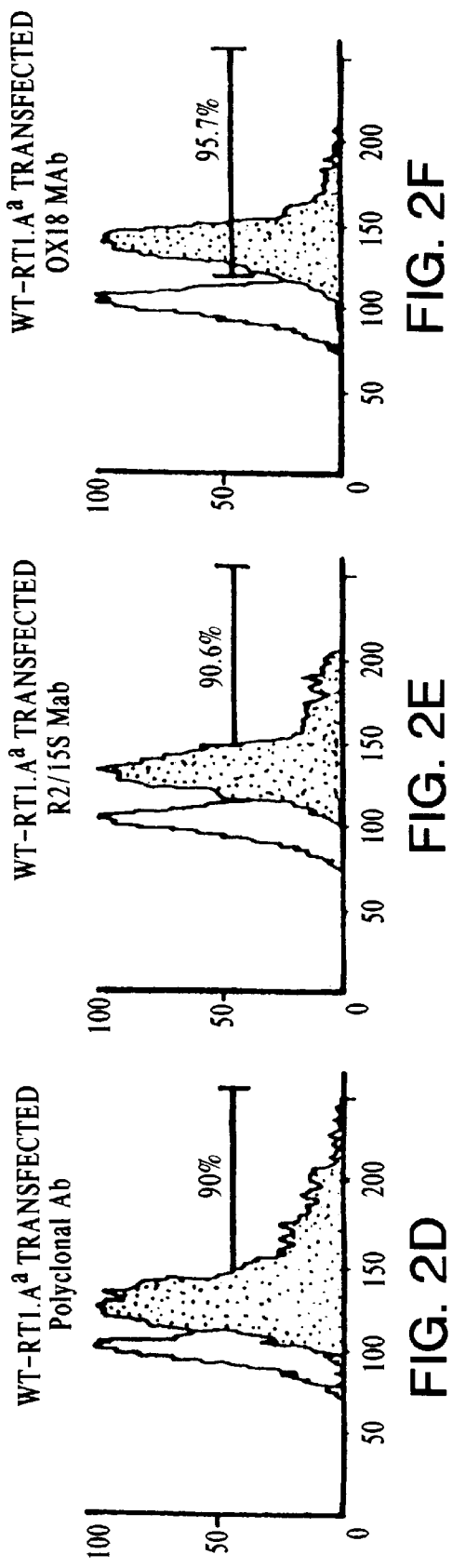

```
                  5   L   R   Y   F   Y   T   A   V   S   R   P   G   L   G   E   P   R   F   I   A   24
WT-RT1.Aa        94  ctg cgg tat ttc tac acc gcc gtg tcc cgg ccc ggc ctc ggg gag ccc cgg ttc atc gct  153
                                                              R
nHLA-A2.1-RT1.Aa                                             cgc
                      M                                        
                     atg ...                                   
                 58   E   Y   W   E   Q   Q   T   R   I   A   K   E   W   E   Q   Y   R   V   D   77
WT-RT1.Aa       253  gag tat tgg gag cag cag aca cgg atc gcc aag gaa tgg gag cag tac cga gtg gac  312
                      D                   R   E               Q                       G       S
[a1u]-RT1.Aa         gac ...             agg gag             cag aaa                  gga     agc
                 78   L   R   T                                               N
WT-RT1.Aa       313  ctg agg acc ...                                         aat
                      N
[a1u]-RT1.Aa         aat
                 97   E   M   Y   G   C   D   V   G   S   D   G   S   L   L   R   G   Y   R   Q   D   116
WT-RT1.Aa       370  gag atg tat ggc tgt gac gtg ggg tcg gac ggg agc ctc ctc cgc gga tat agg cag gac  429
                                          T
[a2u]-RT1.Aa                             aca
                143   T   R   N   K   W   E   R   A   Y   A   E   R   L   R   A   Y   L   E   G   162
WT-RT1.Aa       508  acc cgg aac aag tgg gag cgg gct tat gca gag aga ctc agg gcc tac ctg gag ggc  567
                      R                        D           G   V
[a2u]-RT1.Aa         agg ...                  gat         gat att
                163   T   C   V   E   W   L   S   R   Y   L   E   L   G   K   E   T   L   L   R   S   182
WT-RT1.Aa       568  acg tgt gtg gag tgg ctc agc aga tac ctg gag ctc ggg aag gag aca ctg ctg cgc tca  627
                                          R                                       H                   L
[a2u]-RT1.Aa                             cgc                                     cac                 tta
```

FIG. 6

SEQUENCE LISTING

<160> NUMBER OF SEQ ID NOS: 24

<210> SEQ ID NO 1
<211> LENGTH: 23
<212> TYPE: DNA
<213> ORGANISM: rat
<220> FEATURE:
<223> OTHER INFORMATION: Description of Artificial Sequence: PCT primer

<400> SEQUENCE: 1
caggaattcc gggatctcag atg                                              23

<210> SEQ ID NO 2
<211> LENGTH: 44
<212> TYPE: DNA
<213> ORGANISM: rat
<220> FEATURE:
<223> OTHER INFORMATION: Description of Artificial Sequence: PCT primer

<400> SEQUENCE: 2
gccgggccgg gacacggagg tgaagaaata ccgcatcgag tgtg                       44

<210> SEQ ID NO 3
<211> LENGTH: 28
<212> TYPE: DNA
<213> ORGANISM: rat
<220> FEATURE:
<223> OTHER INFORMATION: Description of Artificial Sequence: PCT primer

<400> SEQUENCE: 3
cgtgtcccgg cccggccgcg gggagccc                                         28

<210> SEQ ID NO 4
<211> LENGTH: 52
<212> TYPE: DNA

```
<213> ORGANISM: rat
<220> FEATURE:
<223> OTHER INFORMATION: Description of Artificial Sequence: PCT primer

<400> SEQUENCE: 4
ctgctcgttt cccttggctt tctgtgtctc cctctcccaa tagtccggcc cc              52

<210> SEQ ID NO 5
<211> LENGTH: 51
<212> TYPE: DNA
<213> ORGANISM: rat
<220> FEATURE:
<223> OTHER INFORMATION: Description of Artificial Sequence: PCT primer

<400> SEQUENCE: 5
gccaagggaa acgagcagaa ttaccgagtg agcctgagga atctgcgcgg c               51

<210> SEQ ID NO 6
<211> LENGTH: 32
<212> TYPE: DNA
<213> ORGANISM: rat
<220> FEATURE:
<223> OTHER INFORMATION: Description of Artificial Sequence: PCT primer

<400> SEQUENCE: 6
ccacgtcaca gccatacatc ctctggatgg tg                                    32

<210> SEQ ID NO 7
<211> LENGTH: 31
<212> TYPE: DNA
<213> ORGANISM: rat
<220> FEATURE:
<223> OTHER INFORMATION: Description of Artificial Sequence: PCT primer

<400> SEQUENCE: 7
gtatggctgt gacgtgggga cggaggggag c                                     31

<210> SEQ ID NO 8
<211> LENGTH: 20
<212> TYPE: DNA
<213> ORGANISM: rat
<220> FEATURE:
<223> OTHER INFORMATION: Description of Artificial Sequence: PCT primer

<400> SEQUENCE: 8
agcccgatcc cacttgttcc                                                  20

<210> SEQ ID NO 9
<211> LENGTH: 38
<212> TYPE: DNA
<213> ORGANISM: rat
<220> FEATURE:
<223> OTHER INFORMATION: Description of Artificial Sequence: PCT primer

<400> SEQUENCE: 9
ggaacaagtg ggatcgggct ggtgttgcag agagactc                              38

<210> SEQ ID NO 10
<211> LENGTH: 59
<212> TYPE: DNA
<213> ORGANISM: rat
<220> FEATURE:
<223> OTHER INFORMATION: Description of Artificial Sequence: PCT primer

<400> SEQUENCE: 10
gggggatcta agcgcagcag tgtctccttc ccgtgctcca ggtatctgcg gagccactc       59
```

```
<210> SEQ ID NO 11
<211> LENGTH: 20
<212> TYPE: DNA
<213> ORGANISM: rat
<220> FEATURE:
<223> OTHER INFORMATION: Description of Artificial Sequence: PCT primer

<400> SEQUENCE: 11
ctgctgcgct tagatccccc                                              20

<210> SEQ ID NO 12
<211> LENGTH: 26
<212> TYPE: DNA
<213> ORGANISM: rat
<220> FEATURE:
<223> OTHER INFORMATION: Description of Artificial Sequence: PCT primer

<400> SEQUENCE: 12
cgataagctt gatatccgaa ttccgg                                       26

<210> SEQ ID NO 13
<211> LENGTH: 20
<212> TYPE: PRT
<213> ORGANISM: rat

<400> SEQUENCE: 13

Leu Arg Tyr Phe Tyr Thr Ala Val Ser Arg Pro Gly Leu Gly Glu Pro
 1               5                  10                  15

Arg Phe Ile Ala
            20

<210> SEQ ID NO 14
<211> LENGTH: 60
<212> TYPE: DNA
<213> ORGANISM: rat

<400> SEQUENCE: 14
ctgcggtatt tctacaccgc cgtgtcccgg cccggcctcg gggagccccg gttcatcgct   60

<210> SEQ ID NO 15
<211> LENGTH: 60
<212> TYPE: DNA
<213> ORGANISM: rat

<400> SEQUENCE: 15
atgcggtatt tcttcacctc tgtgtcccgg cccggccgcg gggagccccg gttcatcgct   60

<210> SEQ ID NO 16
<211> LENGTH: 20
<212> TYPE: PRT
<213> ORGANISM: rat

<400> SEQUENCE: 16

Met Arg Tyr Phe Phe Thr Ser Val Ser Arg Pro Gly Arg Gly Glu Pro
 1               5                  10                  15

Arg Phe Ile Ala
            20

<210> SEQ ID NO 17
<211> LENGTH: 23
<212> TYPE: PRT
<213> ORGANISM: rat
```

-continued

<400> SEQUENCE: 17

Glu Tyr Trp Glu Gln Gln Thr Arg Ile Ala Lys Glu Trp Glu Gln Ile
1               5                   10                  15

Tyr Arg Val Asp Leu Arg Thr
            20

<210> SEQ ID NO 18
<211> LENGTH: 69
<212> TYPE: DNA
<213> ORGANISM: rat

<400> SEQUENCE: 18
gagtattggg agcagcagac acggatcgcc aaggaatggg agcagattta ccgagtggac      60
ctgaggacc                                                             69

<210> SEQ ID NO 19
<211> LENGTH: 69
<212> TYPE: DNA
<213> ORGANISM: rat

<400> SEQUENCE: 19
gactattggg agagggagac acagaaagcc aagggaaacg agcagaatta ccgagtgagc      60
ctgaggaat                                                             69

<210> SEQ ID NO 20
<211> LENGTH: 23
<212> TYPE: PRT
<213> ORGANISM: rat

<400> SEQUENCE: 20

Asp Tyr Trp Glu Arg Glu Thr Gln Lys Ala Lys Gly Asn Glu Gln Asn
1               5                   10                  15

Tyr Arg Val Ser Leu Arg Asn
            20

<210> SEQ ID NO 21
<211> LENGTH: 180
<212> TYPE: DNA
<213> ORGANISM: rat

<400> SEQUENCE: 21
gagatgtatg gctgtgacgt ggggtcggac gggagcctcc tccgcggata taggcaggac      60
acccggaaca gtgggagcg ggctcgttat gcagagagac tcagggccta cctggagggc     120
acgtgtgtgg agtggctcag cagataccta gagctcggga aggagacact gctgcgctca     180

<210> SEQ ID NO 22
<211> LENGTH: 60
<212> TYPE: PRT
<213> ORGANISM: rat

<400> SEQUENCE: 22

Glu Met Tyr Gly Cys Asp Val Gly Ser Asp Gly Ser Leu Leu Arg Gly
1               5                   10                  15

Tyr Arg Gln Asp Thr Arg Asn Ser Trp Glu Arg Ala Arg Tyr Ala Glu
            20                  25                  30

Arg Leu Arg Ala Tyr Leu Glu Gly Thr Cys Val Glu Trp Leu Ser Arg
        35                  40                  45

Tyr Leu Glu Leu Gly Lys Glu Thr Leu Leu Arg Ser
    50                  55                  60

```
<210> SEQ ID NO 23
<211> LENGTH: 180
<212> TYPE: DNA
<213> ORGANISM: rat

<400> SEQUENCE: 23
gggatgtatg gctgtgacgt ggggacggac gggagcctcc tccgcggata taggcaggac        60
acccggaaca agtgggagcg ggctggtgtt gcagagagac tcagggccta cctggagggc       120
acgtgtgtgg agtggctccg cagatacctg gagcacggga aggagacact gctgcgctta       180

<210> SEQ ID NO 24
<211> LENGTH: 60
<212> TYPE: PRT
<213> ORGANISM: rat

<400> SEQUENCE: 24

Arg Met Tyr Gly Cys Asp Val Gly Thr Asp Gly Ser Leu Leu Arg Gly
 1               5                  10                  15

Tyr Arg Gln Asp Thr Arg Asn Lys Trp Asp Arg Ala Gly Val Ala Glu
            20                  25                  30

Arg Leu Arg Ala Tyr Leu Glu Gly Thr Cys Val Glu Trp Leu Arg Arg
        35                  40                  45

Tyr Leu Glu His Gly Lys Glu Thr Leu Leu Arg Leu
    50                  55                  60
```

CHIMERIC MHC CLASS I ANTIGENS FOR INDUCING ALLOGRAFT TOLERANCE

This is a continuation of application Ser. No. 08/245,337 filed on May 18, 1994 abandoned.

This invention was made with government support under Grant AI22664, awarded by the National Institutes of Health. The government has certain rights in the invention.

FIELD OF THE INVENTION

This invention relates to recombinant major histocompatibility complex (MHC) molecules, and specifically to chimeric MHC Class I molecules engineered to induce allograft tolerance. This invention also relates to methods for inducing tolerance to a transplanted allograft by administering to the transplant recipient a chimeric MHC Class I molecule having self-type regulatory domains and donor-type immunogenic domains.

BACKGROUND OF THE INVENTION

The major histocompatibility complex (MHC) includes histocompatibility antigens, polymorphic membrane glycoproteins found on the surface of nearly all cells. One individual simultaneously expresses polymorphic forms from a large pool of alleles in the population. Rejection of foreign tissue transplants is initiated by antibody and cytotoxic lymphocyte (CTL) recognition of Class I histocompatibility antigens. T-cell receptors only recognize foreign antigens that are associated with a particular histocompatibility antigen molecule.

As known to one of skill in the art, MHC molecules bind an intracellular foreign peptide antigen, transport the bound antigen to the surface of the cell membrane, and present the antigen for recognition by T-cells. T-cell recognition of antigen-bound MHC molecules then initiates a cascade of events in the immune response.

In organ transplantation, despite major advances in surgical techniques and the development of new drugs, the majority of transplant recipients remain at high risk for rejection. Currently available therapies to prevent rejection rely on broad spectrum immunosuppressive drugs such as cyclosporin A (CsA), which must be taken through out the individual's life. The cumulative effects of such long-term immunosuppression include opportunistic infections, cancers, and drug-specific toxicity. It would be of great utility to develop a therapeutic system administered only in the perioperative period which could thereby avoid the long-term effects of immunosuppression.

Prior attempts to alleviate organ transplant rejection using the MHC molecule have included administration of whole donor cells, which express donor-type MHC antigens. This method requires pre-operative administration of the alloantigen, and thus has only limited clinical applicability because of the need for donor-identification well in advance of the time of transplantation. It would be highly desirable to develop an effective therapeutic system which could be administered at the time of transplantation.

SUMMARY OF THE INVENTION

It has now been found that the MHC Class I molecule includes specific functional domains important in the generation of an immune response. A dominant allogenic epitope was mapped to the helical portion of the alpha-1 domain and a sub-dominant allogeneic epitope was mapped to the N-terminus of the alpha-1 domain of MHC Class I molecules. Unexpectedly, the alpha-2 domain was shown to lack immunogenic sequences, but to have an important regulatory role in recognition of a foreign antigen. The substitution of donor-type immunodominant alpha-1 helical epitope for the wild-type (recipient) immunodominant epitope converted the immunogenic MHC Class I molecule to a tolerogen when the flanked by recipient-type alpha-1N-terminus and alpha-2 domain sequences. Treatment of transplant recipients with extracts of transfected cells bearing these "quasi-self" chimeric MHC Class 1 molecules together with a 7-day cyclosporine (CsA) course induced donor-specific transplantation tolerance. This chimeric molecule provides a clinically relevant system for the induction of allograft tolerance.

BRIEF DESCRIPTION OF THE FIGURES

FIG. 2 is a graphic representation of WT-RT1.A$^a$ detection on the cell surfaces of control and transfected 7316A BUF hepatoma cells by exposure to a fluoresceinated rabbit anti-rat IgG antibody (1:250 dilution; non-shaded region) or with pre-coated anti-RT1$^a$ antibody (shaded region). The percent of stained cells is shown in each figure.

FIG. 2A shows non-transfected hepatoma cells that were exposed to polyclonal anti-RT1$^a$ antibody.

FIG. 2B shows non-transfected hepatoma cells that were exposed to R2/15S anti-rat RT1.A$^a$ Class I polymorphic monoclonal antibody.

FIG. 2C shows non-transfected hepatoma cells that were exposed to MRC OX18 anti-rat RT1A class I monomorphic monoclonal antibody.

FIG. 2D shows hepatoma cells transfected with WT-RT1.A$^a$ that were exposed to polyclonal anti-RT1$^a$ antibody.

FIG. 2E shows hepatoma cells transfected with WT-RT1.A$^a$ that were exposed to R2/15S anti-rat RT1.A$^a$ Class I polymorphic monoclonal antibody.

FIG. 2F shows hepatoma cells transfected with WT-RT1.A$^a$ that were exposed to MRC OX18 anti-rat RT1A class I monomorphic monoclonal antibody.

FIG. 5A shows production of N$^{HLA-A2.1}$-RT1.A$^a$: The overlapping products of PCR #1, 140 base pairs (lane 2) and PCR #2, 1490 base pairs (lane 3) were SOEd in PCR #3 (lane 4).

FIG. 5B shows production of α-1h$^u$-RT1.A$^a$: The overlapping products of PCR #1, 300 base pairs (lane 2) and PCR #2, 1310 base pairs (lane 3) were SOEd in PCR #3 (lane 4).

FIG. 5C shows production of α-2d$^u$-RT1.A$^a$: Four overlapping PCR products 400, 150, 120 and 990 b.p. (lanes 2–5) were SOEd together in PCR #5 (lane 6).

FIG. 6 shows the deduced amino acid sequence of wild-type RT1.A$^a$ (SEQ ID NO. 13) and the nucleotide sequence of wild-type RT1.A$^a$ (SEQ. ID NO. 14) compared to the nucleotide sequence of the chimera N$^{HLA-A2.1}$-RT1.A$^a$ (SEQ. ID NO. 15) and the deduced amino acid sequence of chimera N$^{HLA-A2.1}$-RT1.A$^a$ (SEQ. ID NO. 16), the deduced amino acid sequence of wild-type RT1.A$^a$ (SEQ ID NO. 17) and nucleotide sequence of wild-type RT1.A$^a$ (SEQ. ID NO. 18) compared to nucleotide sequence of the α-1h-RT1.A$^a$ chimera (SEQ. ID NO. 19) and the deduced amino acid sequence of the α-1h-RT1.A$^a$ chimera (SEQ. ID NO. 20), and the nucleotide sequence of wild-type RT1.A$^a$ (SEQ. ID .NO. 21) and the deduced amino acid sequence of wild-type RT1.A$^a$ (SEQ ID NO. 22) compared to nucleotide sequence of the α-2d$^u$-RT1.A$^a$ chimera (SEQ. ID NO. 23) and the deduced amino acid sequence of the α-2d$^u$-RT1.A$^a$ chimera (SEQ. ID NO.24). Full length cDNAs were sequenced in both directions. The shown sequences represent only the changed amino acid residues and the corresponding nucleotide changes (underlined). The dots indicate no alterations from the WT-RT1.A$^a$ sequences.

FIG. 7 is a graph showing detection of chimeric RT1.A$^a$ on the cell surfaces of transfected BUF hepatoma cells. The RT1.A$^a$ cDNAs were exposed to fluoresceinated rabbit anti-rat IgG antibody (1:250 dilution) without (non-shaded) or with (shaded) pre-coating with polyclonal anti-RT1.A$^a$ (1:8 dilution) antibody.

FIG. 10A shows the presence of IgG-binding alloantibodies. Data are presented as mean channel shift.

FIG. 10B shows the presence of IgM-binding alloantibodies. Data are presented as mean channel shift.

FIG. 10C shows the presence of anti-ACI cytotoxic alloantibodies. Data are presented as % specific lysis.

DETAILED DESCRIPTION OF THE PREFERRED EMBODIMENT

MHC Class I Molecules

Figure 1:
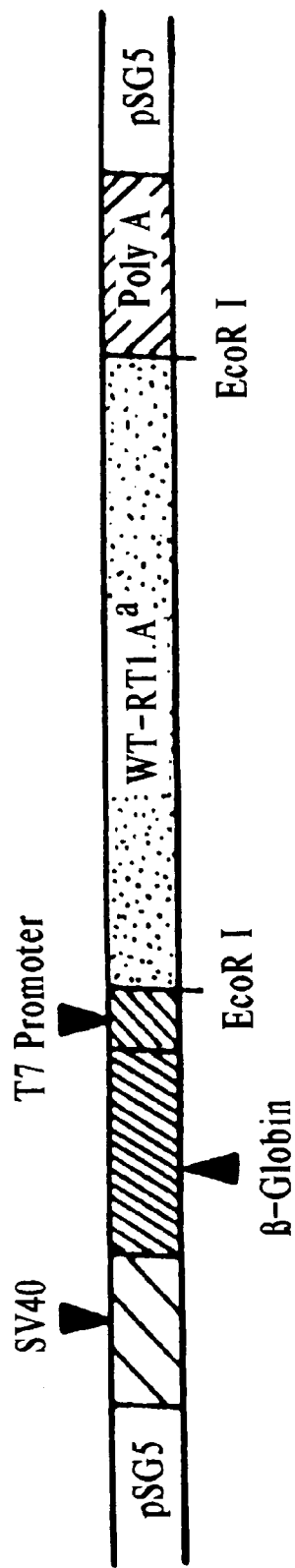
FIG. 1 is a diagrammatic representation of an expression vector for expression of WT-RT1.A$^a$ in BUF hepatoma cells. The gene encoding WT-RT1.A$^a$ was subcloned in the proper orientation at the EcoR I site of the pSG5 mammalian expression vector containing the SV40 promotor and enhancer.

Class I transplantation antigens of the major histocompatibility complex (MHC) are cell surface glycoproteins which present antigens to cytotoxic T-cells. They are heterodimeric and composed of a polymorphic, MHC-encoded, approximately 45 KD heavy chain, which is non-covalently associated with an approximately 12 KD beta-2 microglobulin (beta-2m) light chain. The H-2 system of the mouse and the HLA system of the human, as well as the RT1 system of the rat have been studied. Among the several allelic types of Class I molecules only certain ones affect graft survival in each species (HLA-A, B in humans; H-2K, D in mice; and RT.1A in rat).

The extracellular portion of the MHC Class I heavy chain is divided into three domains, alpha-1, alpha-2, and alpha-3, each approximately 90 amino acids long and encoded on separate exons. The alpha-3 domain and beta-2m are relatively conserved and show amino-acid sequence homology to immunoglobulin constant domains. The polymorphic alpha-1 and alpha-2 domains show no significant sequence homology to immunoglobulin constant or variable regions, but do have weak sequence homology to each other. The membrane-distal polymorphic alpha-1 (approximately 90 amino acids) and alpha-2 (approximately 92 amino acids) domains each include four anti-parallel, beta-pleated sheets bordered by one alpha-helical regions, (the first from the alpha-1 and the second from the alpha-2 domain). The alpha-2 domain is attached to the less-polymorphic, membrane-proximal alpha-3 (approximately 92 amino acids) domain which is followed by a conserved transmembrane (25 amino acids) and an intra-cytoplasmic (approximately 30 amino acids) segment. The rat, mouse, and human Class I MHC molecules are believed to have similar structural characteristics based upon known nucleotide sequences of the various MHC Class I molecules.

For a review of the structure and function of the MHC Class I molecules, see, for example: Matsumura et al., 1992, *Science* 257:927–934; Bjorkman and Parham, 1990, *Annu. Rev. Biochem.*, 59:253–288; and Germain, 1994, *Cell*, 76:287–299.

Immunodominant Epitope

The alpha-1 domain has now been shown to contain an immunodominant, immunogenic epitope in the alpha-1 helical region and a subdominant, N-terminal allogenic determinant. The alpha-2 domain does not contain an immunogenic epitope.

That the immunodominant immunogenic epitope was contained in the alpha-1 helical region was shown by the following experiments. A chimeric mutant of the RT1.A$^a$ molecule was constructed by replacing the alpha-1 helical region with a corresponding alpha-1 helical region of an RT1.A$^u$ gene sequence. The protein produced from this chimeric gene was unable to sensitize RT1$^b$ (BUF) host toward transplanted RT1.A$^a$ bearing ACI grafts. In contrast, the same chimeric peptide did sensitize RT1$^b$ (BUF) host toward WFu allografts which express the RT1.A$^u$ antigen. Additional chimeras which contained the alpha-1$^a$ helical epitope did immunize both BUF and WFu hosts against the ACI grafts.

Subdominant Immunogenic Epitope

The presence of a subdominant immunogenic epitope in the N-terminal segment of the alpha-1 domain was demonstrated by the following experiments: The wild type RT1.A$^a$ gene was altered by replacing the N-terminal epitope (approximately 20 amino acids) with the corresponding N-terminal epitope of the human HLA-A2.1 sequence. This substitution resulted in reduced immunogenicity toward RT1$^a$ (ACI) grafts in WFu hosts, indicating the presence of an immunogenic epitope in the N-terminus. However, the N-terminal$^a$ epitope alone, present in the RT1.A$^a$ chimera having the alpha-1$^a$ helical sequence replaced with the corresponding alpha-1$^u$ helical sequence failed to sensitize either BUF (RT1$^b$) or WFu (RT1$^u$) rats against ACI (RT1$^a$) grafts. The subdominant epitope corresponds to the first beta-strand and loop of the alpha-1 domain.

Regulatory Epitope

In contrast to the alpha-1 domain, the alpha-2 allogenic domain lacked potent immunogenic determinants. This was shown by two experiments: The wild type RT1.A$^a$ gene was altered by replacing the entire alpha-2$^a$ domain with the corresponding alpha-2$^u$ domain sequences. Neither the protein encoded by this chimeric gene nor the protein encoded by the chimeric gene containing alpha-1$^u$ helical sequences were able to immunize BUF (RT1$^b$) recipients toward WFu (RT1$^u$) or ACI (RT1$^a$) heart allografts, respectively.

The flanking of immunogenic epitopes by syngenic sequences directs host immune responses toward unresponsiveness. This observation is based on the result of two experiments. First, WFu (RT1$^u$) hosts injected with transfected cells bearing an N-terminal$^a$ and alpha-1 helical$^a$ immunogenic epitopes together with an alpha-2$^u$ domain sequences were not sensitized toward RT1$^a$ (ACI) allografts. Further, these recipients failed to produce anti-ACI alloantibodies and displayed the presence of negative regulatory T-cells that inhibited the function of allospecific CTLs. The same chimeric molecules did sensitize BUF (RT1$^b$) recipients to accelerate the rejection of ACI (RT1$^a$) hearts. Secondly, ACI recipients treated with transfectants bearing the dominant donor-type alpha-1$^u$ helical immunogenic epitope flanked by recipient-type N-terminala and alpha-2$^a$ sequences prolonged (WFu) RT1$^u$ heart allograft survival. This coincided with reduced fTc directed against WFu alloantigens. The same chimeric molecule induced accelerated rejection of WFu (RT1$^u$) hearts in BUF (RT1$^b$) recipients. This effect indicates that donor-type immunogenic epitopes displayed on recipient-type Class I molecules become tolerogenic.

Chimera Induced Tolerance

The role of the specific Class I MHC alloantigens in induction of unresponsiveness toward allografts is clear from experiments in mice. Extracts of transfected cells bearing the alpha-1$^u$-helix flanked by recipient N-terminal$^a$ and alpha-2$^a$ sequences were injected once via the portal vein at the time of transplantation (day 0) in conjunction with a seven-day course of CsA therapy. This treatment induced donor-specific tolerance to WFu (RT1$^u$) heart allografts in 80% of ACI (RT.1$^a$) recipients. In contrast, extracts from wild type RT1.A$^a$, WFu Class I RT1u$^a$ bearing hepatocytes, and chimeric molecules having N-terminus antigen substitution or alpha-2 domain substitution were ineffective in preventing graft rejection. Thus, modification of Class I MHC alloantigens was used to develop chimeric Class I molecules that induced a negative immune response to intact wild type antigens. Tolerance induction using chimeric (quasi-self) Class I molecules represents a novel, clinically applicable approach to preventing graft rejection.

Useful Chimeras

Useful chimeric molecules of the present invention are MHC Class I antigens having a recipient-type N-terminal region of the alpha-1 domain, recipient-type alpha-2 domain, and a donor-type alpha-1 helical region. It is understood by one of skill in the art that the chimeric MHC Class I molecules or genes encoding them may be modified or altered without significantly changing the immunogenic and regulatory epitopes and thus without altering the function of the chimeras of the present invention. Useful chimeras of the present invention, in three dimensional form, preferably present a surface sufficient for binding and presenting a foreign peptide. The chimeric MHC Class I molecules of the present invention include a donor-type immunogenic determinant (alpha-1h), an recipient type N-terminal immunogenic determinant (alpha-1N), and a recipient-type alpha-2 determinant.

Useful chimeric molecules of the present invention may be prepared and screened in the following manner. Chimeric genes may be prepared by recombinant methods known to those of skill in the art. A preferred method is the PCR-based method of gene splicing with overlap extension described in Example 2. A gene encoding a specified MHC Class I antigen is altered to replace the immunodominant α-1h epitope with the corresponding immunodominant α-1h epitope of a different MHC Class I molecule. Preferably, the conserved epitope is of a recipient's MHC Class I type and the sequences replacing the immunodominant epitope are derived from a specified donor's MHC Class I type. Cells transfected with the genes encoding the chimeric proteins express these proteins, which are extracted, e.g., with three molar KCl. Approximately 10 milligrams of the extract containing the chimeric proteins is injected into the portal vein of a model recipient (e.g. rat) at the time of donor organ transplantation (day 0). Transplanted animals are also given a seven day oral CsA course (10 mg/kg, days 0–6). Mean animal survival rate is calculated for test and control animals. Useful chimeric molecules of the present invention are those which can induce donor-specific transplantation tolerance.

Specific chimeric MHC Class I genes encoding MHC Class I proteins that produce a tolerogenic effect include gene sequences encoding the recipient's-type N-terminal portion of the α-1 domain (approximately 20 amino acids) and the α-2 domain and sequences encoding the donor's-type helical region of the α-1 domain. Preferably, the substituted donor sequences include the polymorphic region of the α-1 helical region.

The chimeric MHC Class I molecules of the present invention may be administered to transplant recipients preferably at the time of transplantation, by methods known in the art. Preferably, the molecules are injected, most preferably intravenously. The chimeric molecules may be administered as purified glycoprotein, as extracts or as whole cells expressing the molecules. The appropriate dose and administration regimen may be determined by the administering physician by known methods.

In a preferred embodiment, extracts of cells transfected with genes encoding the chimeric molecules are administered peri-operatively together with a seven day course of CsA therapy.

EXAMPLES

Example 1

CHARACTERIZATION OF THE EFFECT OF WILD TYPE-RT1.$A^a$

Wild type RT1.$A^a$ cDNA was obtained from J. Howard (Rada et al., 1990, *PNAS USA*, 87:2167–2171) was subcloned in the proper orientation at the ECORI site of the mammalian expression vector pSG5 containing the SV40 promoter and enhancer (Stratagene, LaJolla, Calif.). This vector was co-transfected into BUF ($RT1^b$) Morris hepatoma 7316 A cells (Masuji et al., *Acta Med. Okyama*, 28:281–293, 1974) with pSV2-NEO containing the neomycin resistance gene, using the lipofectin reagent (GIBCO, Grand Island, N.Y.; Felinger et al., 1987). Lipofectin (25μl) plasmid DNA (10 μ pSG5-RT1.$A^a$:pSU2NEO, 10:1) complexes were added to 2×105 cells in 4 ml serum-free medium (complete RPMI, Sigma, St. Louis, Mo.) in 60 ml culture dishes. Following a six hour incubation at 37° C., the medium was replaced with ten percent Fetal Calf Serum-RPMI. After 48 hours of further incubation, stable transfectants were selected by the addition of 400 μg/ml (final concentration) Geneticin (G418, GIBCO, Grand Island, N.Y.) to the culture medium surviving colonies were expanded and analyzed for surface expression of RT1.$A^a$.

The transfected cells were analyzed by FACS to detect RT1.$A^a$ on the cell surfaces by exposing the cells to a fluorescinated rabbit anti-rat IgG antibody (1:250 dilution) or by precoating with specific antibodies.

Flow cytometry analysis

To detect surface expression of wild-type RT1.$A^a$ on transfected BUF ($RT1^b$) hepatoma cells, transfected and non-transfected BUF hepatoma cells were suspended in Hank's Balanced Salt Solution (HBSS; Sigma, St. Louis, Mo.) supplemented with 5% fetal calf serum (FCS). Approximately $3\times10^3$ cells were incubated at 4° C. for 30 minutes in 50 μl of 1:4, 1:8 and 1:16 dilution of polyclonal BUF ($RT1^b$) antibodies raised against WT-RT1.$A^a$ or 50 μl of 1:150 dilution of R2/15S anti-rat RT1.$A^a$ class I polymorphic monoclonal antibody (Bioproducts for Science, Indianapolis, Ind.) or anti-rat RT1.A class monomorphic monoclonal antibody MRC OX 18 (Bioproducts for Science, Indianapolis, Ind.) After washing, 50 μl of 1:250 dilution of fluorescein (FITC)-conjugated rabbit anti-rat Ig (Zymed labs, San Francisco, Calif.) was added to the cells. Following a second incubation, cells were washed and fixed with 1.5% paraformaldehyde. Cells stained only with FITC rabbit anti-rat Ig were used for measurement of background non-specific fluorescence. Analysis was performed on a Becton-Dickinson Laser Flow Cytometry System (Mountain View, Calif.). Data are presented as percent of cells with positive staining calculated as the difference between the sample's fluorescence and background staining.

As shown in FIG. 2, FACS analysis of wild type RT1.$A^a$ stable transfectants demonstrated enhanced (greater than 90%) positive staining with anti-$RT1^a$ polyclonal antibody or specific anti-RT1.$A^a$ Class I RT2/15S monoclonal antibody. In addition, staining with the anti-rat RT1A class monomorphic monoclonal antibody MRC OX18 demonstrated greater total surface expression of Class I molecules on transfected cells than on non-transfected cells.

Adult male inbred WFu ($RT1^a$) rats (Harlan Sprague Dawley, Indianapolis, Ind.) were injected with $1\times10^5$–$2\times10^7$ control or transfected cells 7 days prior to AC1 heart grafts. The mean survival time of the grafts was calculated.

Cardiac transplantation

Heterotopic cardiac transplants were harvested from donor rats (Harlan Sprague Dawley, Indianapolis, Ind.) and placed intra-abdominally as previously described (Ono and Lindsey, 1969, *J. Thoracic Cardiovasc. Surg.* 51: 225–229).

Donor hearts were perfused through the aorta with chilled heparinized cardioplegic solution prior to retrieval by ligation of the vena cava and pulmonary veins after the recipients were anaesthetized with ketamine hydrochloride (Parke-Davis, Morris Plains, N.J.; 0.1 mg/100 g weight). Infrarenal vena cava and aortic microvascular anastomosis to donor pulmonary artery and aorta were performed using 8–0 nylon sutures (Ethicon, Somerville, N.J.). Cold ischemia time was less than 45 minutes. Cardiac activity was assessed by abdominal palpation. Data are presented as mean survival time (MST)±S.D. and compared using the t-test; a value of P<0.05 indicated statistical significance.

Figure 3:
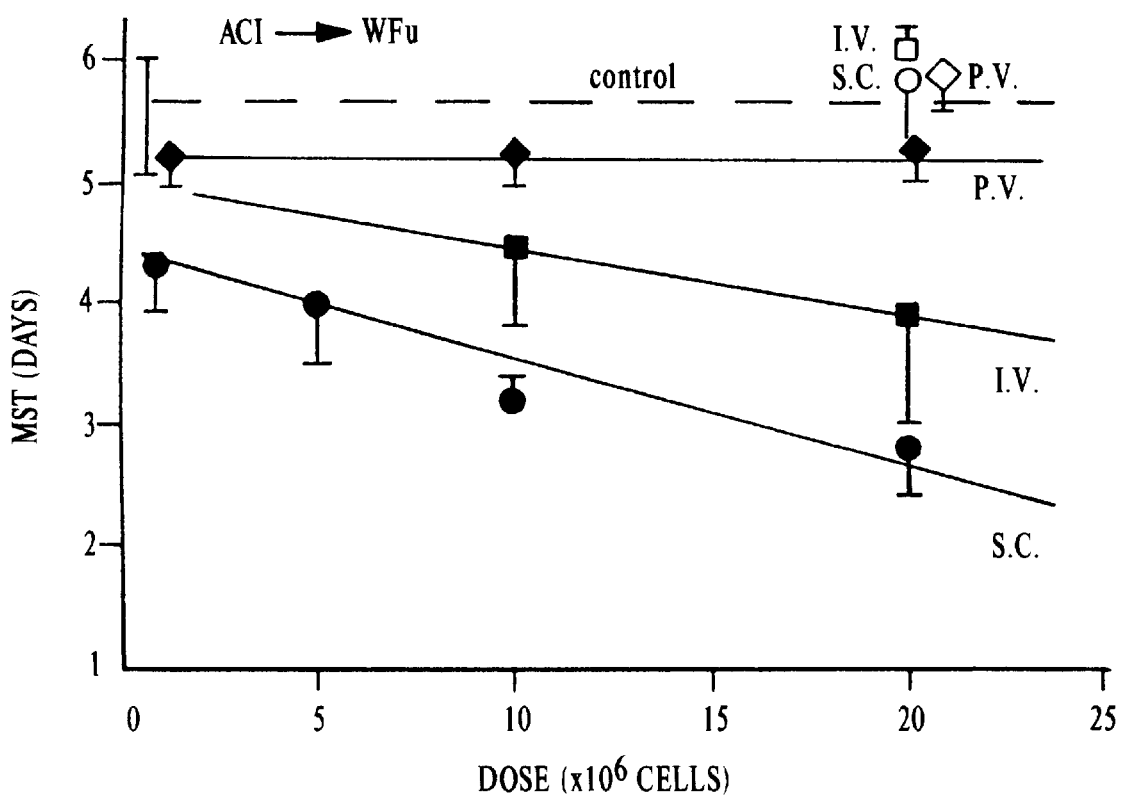
FIG. 3 is a graphic representation of dose-dependent immunization toward ACI (RT1$^a$) by WT-RT1.A$^a$ transfectants. WF (RT1$^u$) rats were injected with $10^5$ to $2\times10^7$ cells 7 days prior to ACU heart grafts. The dashed horizontal line represents the mean survival time of ACI grafts in untreated WF recipients. Subcutaneous injection (filled circles); intravenous injection (filled squares); and portal vein injection (filled diamonds) are shown. Normal hepatoma cells given by subcutaneous administration (open circles); intravenous injection (open squares) or by the portal vein (open diamonds) are also shown.

Subcutaneous injection of WFu rats approximately four to six weeks old, weighing about 160–200 g ($RT1^u$) (Helen Sprague-Dowdy, Indianapolis, Ind.) with $1-2\times10^7$ wild type $RT1.A^a$-transfected BUF hepatoma cells, but not control, non-transfected BUF ($RT1^b$) hepatoma cells, seven days prior to ACI ($RT1^a$) heart allograft challenge shortened the mean survival time of transplanted animals from 5.4±0.5 days to 3±0.0 days or 2.8±0.4 days, respectively (p<0.001). Intravenous delivery was less immunogenic, and the portal vein route was ineffective. These data are shown in FIG. 3.

Example 2
THE PRODUCTION AND CHARACTERIZATION OF CHIMERIC $RT1.A^a$ CLASS I ANTIGENS The polyinerase chain reaction (PCR)-based method of gene splicing with overlap extension (gene SOEing) was used to produce three chimeric molecules using a panel of primers. This method is described in Horton et al., *Biotechniques*, 8:528 (1990), "Gene Splicing by Overlap Extension: Tailor-Made Genes Using the Polymerase Chain Reaction," which is hereby incorporated by reference for all purposes.

The plasmid pBS3.3/1 (Rada et al., 1990, *PNAS USA*, 87:2167–2171) containing wild-type $RT1.A^a$ cDNA, served as a template for PCR amplification reactions between 5' and 3' flanking "outside primers" A and L (see Table 1 for sequence data) that contain the Eco R I restriction site and two internal overlapping "SOEing" primers, which contained the base substitutions. The first PCR reaction used one µl of the 5' outside primer (500 ng), one µl of the first internal primer (500 ng), one µl dNTP (25 mM), one µl DNA template (one µg), ten µl of 10× hot tub DNA polymerase buffer, one µl of hot tub DNA polyerase (Amersham, Arlington, Ill.), and 85 µl $dH_2O$. A second PCR reaction used the second internal primer and the 3' flanking outside primer. The PCR reactions were covered with mineral oil and subjected to two cycles of:

one minute denaturation at 94° C.;
two minutes annealing at 53° C.; and
three minutes elongation at 72° C.,
followed by 23 cycles of:
one minute denaturation at 94° C.;
two minute annealing at 59° C.; and
three minute elongation at 72° C., and ending with ten minute elongation at 72° C.

The two PCR products were electrophoresed in low melting agarose gels to yield the approximately sized DNA bands for excision and melting at 60° C. A third SOEing PCR reaction used the two outside flanking primers with five microliters from the melted gel slices of the first and second PCR reactions as DNA templates to yield a 1.6 kb $RT1.A^a$ DNA fragment, which was excised, eluted, ethanol precipitated, washed with 70% ethanol and dissolved in dH2O.

Primers used in these reactions are shown in Table 1:

TABLE 1

| CODE | SEQ. I.D. | NUCLEOTIDE SEQUENCE(5'→3') |
|---|---|---|
| A | 1 | CAGGAATTCCGGGATCTCAGATG |
| B | 2 | GCCGGGCCGGGACACGGAGGTGAAGAAATACCGCATCGAGTGTG |
| C | 3 | CGTGTCCCGGCCCGGCCGCGGGGAGCCC |
| D | 4 | CTGCTCGTTTCCCTTGGCTTTCTGTGTCTCCCTCTCCCAATAGTCCGGCCCC |
| E | 5 | GCCAAGGGAAACGAGCAGAATTACCGAGTGAGCCTGAGGAATCTGCGCGGC |
| F | 6 | CCACGTCACAGCCATACATCCTCTGGATGGTG |
| G | 7 | GTATGGCTGTGACGTGGGGACGGAGGGGAGC |
| H | 8 | AGCCCGATCCCACTTGTTCC |
| I | 9 | GGAACAAGTGGGATCGGGCTGGTGTTGCAGAGAGACTC |
| J | 10 | GGGGGATCTAAGCGCAGCAGTGTCTCCTTCCCGTGCTCCAGGTATCTGCGGAGCCACTC |
| K | 11 | CTGCTGCGCTTAGATCCCCC |
| L | 12 | CGATAAGCTTGATATCCGAATTCCGG |

Internal primers B, C, D, and E were used to produce the N-terminus substitutions.

Six internal primers: F, G, H, I, J and K, were utilized in four initial separate PCR reactions followed by one SOEing reaction with primers A and L to alter the alpha-2 domain.

Figure 4:
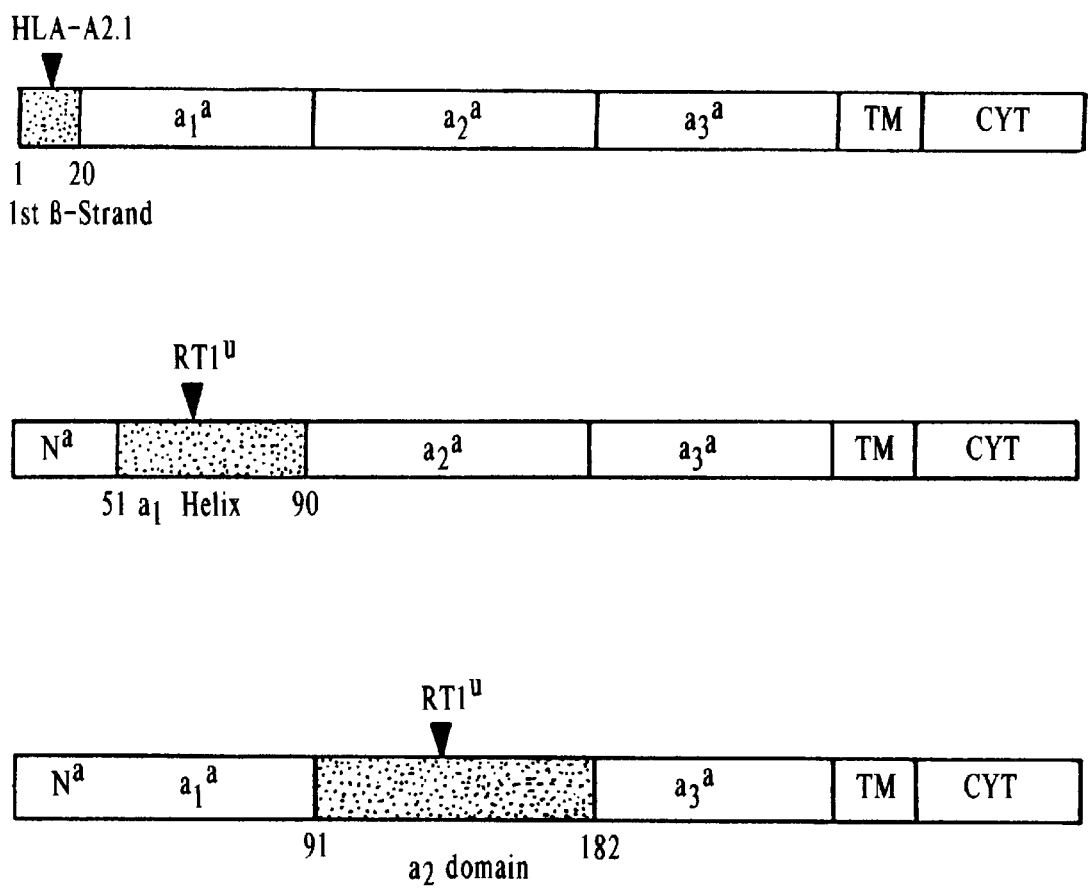
FIG. 4 is a schematic illustration of class I RT1.A$^a$ showing the chimeric substitution sites. N$^{HLA-A2.1}$-RT1.A$^a$ contains four residue changes (at 5, 9, 11, and 17) at the N-terminus which alters the sequence of the first 20 amino acids (first beta-strand and loop) to that of HLA-A2.1. The chimera α-1hu-RT1.A$^a$ contains ten amino acid changes in the α-helix (51–90) of the α-1 domain (at positions 58, 62, 63, 65, 66, 69, 70, 73, 77, and 80) to alter this region to that of RT1.A$^u$. The chimera α-2d$^u$-RT1.A$^a$ has eight amino acid changes along the first beta-strand and the α-helix (at positions 97, 105, 148, 151, 152, 169, 174, and 182) of the α-2 domain (91–182) which changes this domain to that of RT1.A$^u$. TM is the trans-membrane domain and CYT is the cytoplasmic domain.

In these reactions, substitutions were made in the N-terminus (N), alpha-1 helical region (α-1h) or alpha-2 domain (α-2d) of wild type-$RT1.A^a$ cDNA. These gene sequences are schematically diagrammed in FIG. 4, and the constituents of the chimeras produced are shown in Table 2:

TABLE 2

| MHC CLASS I GENE | N-TERMINUS SUB-DOMINANT EPITOPE | α-1 HELICAL DOMINANT EPITOPE | α-2 DOMAIN REGULATORY EPITOPE |
|---|---|---|---|
| WT-$RT1.A^a$ | Rat-a | Rat-a | Rat-a |
| $N^{HLA-A2.1}$-$RT1.A^a$ | HLA | Rat-a | Rat-a |
| $\alpha\text{-}2^u$-$RT1.A^a$ | Rat-a | Rat-a | Rat-u |
| $\alpha\text{-}1h^u$-$RT1.A^a$ | Rat-a | Rat-u | Rat-a |

Figure 5A:
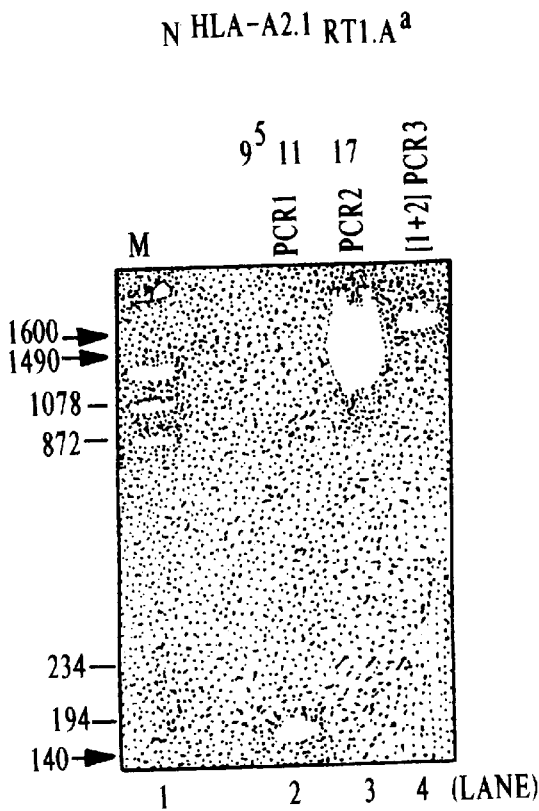
FIGS. 5A–C are a series of photographs showing the production of altered RT1.A$^a$ cDNA by PCR Gene SOEing. The positions of changed amino acids are indicated above each lane.

The plasmid pBS 3.3/1 (Rada et al., *PNAS USA*, 87:2167–2171, 1990) containing the wild type $RT1.A^a$ cDNA was used as a template for PCR amplification reactions between the 5' and 3' flanking outside primers (A and L), each containing an EcoR I site, and two internal overlapping SOEing primers containing the base substitutions. The $N^{HLA-A2.1}$- $RT1.A^a$ mutant bears N-terminal nucleotides encoding the first 20 amino acids of human HLA-A2.1 in the first beta-strand and loop of the alpha-1 domain. Three PCR reactions were used to change nucleotides encoding $Leu^5$ to Met, $Tyr^9$ to Phe, $Ala^{11}$ to Ser and $Leu^{17}$ to Arg, using the internal primers B and C. FIG. 5A shows the products of the first PCR reaction (primers A and B; 140 base pair, lane 2) and the second PCR reaction (primers C and L; 1490 base pairs, lane 3), which were SOEd in the third PCR reaction (primers A and L) to produce the 1.6 kb chimeric cDNA (lane 4).

Figure 5B:
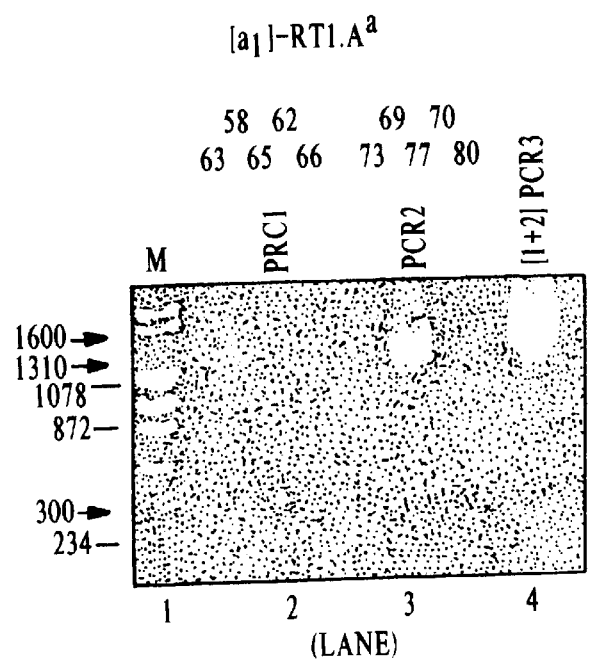

The alpha-1hu $RT1.A^a$ cDNA contained $RT1.A^u$ sequences in the alpha-1 helix (amino acids 51–90), thereby changing $Glu^{58}$ to Asp, $Gln^{62}$ to Arg, $Gln^{63}$ to Glu, $Arg^{65}$ to Gln, $Ile^{66}$ to Lys, $Glu^{69}$ to Gly, $Trp^{70}$ to Asn, $Ile^{73}$ to Asn, $Asp^{77}$ to Ser, and $Thr^{80}$ to Asn by using the internal primers D and E. FIG. 5B shows the first PCR reaction (primers A and D) generated a 300 base pair fragment (lane 2) that was SOEd into the 1310 base pair fragment generated by the second PCR (primers E and L, lane 3) in a third PCR reaction (lane 4).

Figure 5C:
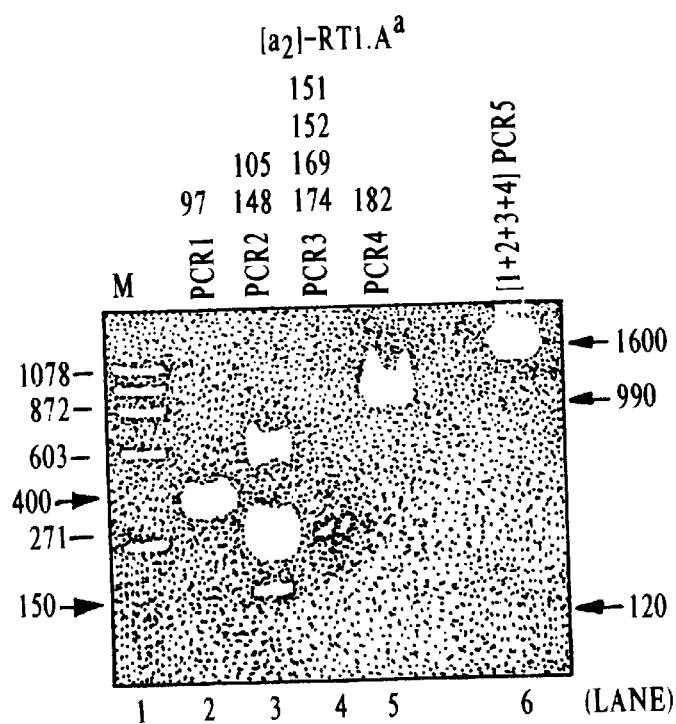
Figure 7A:
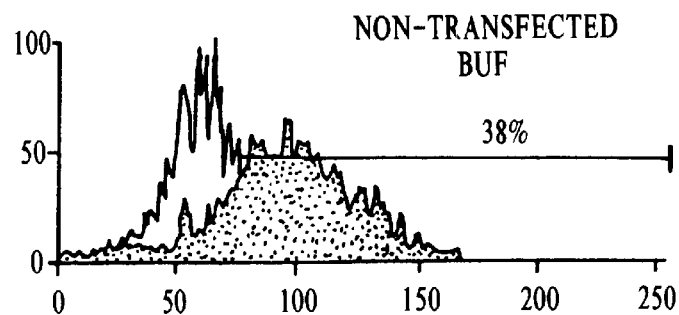
FIG. 7A shows detection of RT1.A$^a$ on non-transfected hepatoma cells.
Figure 7B:
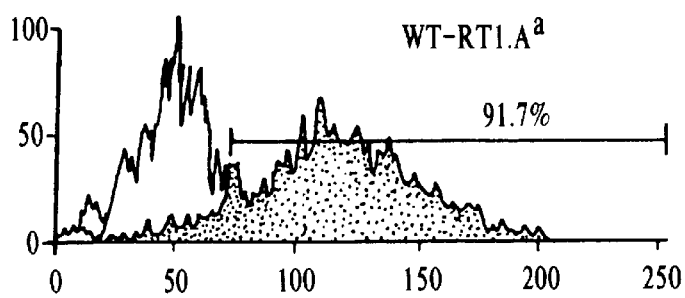
FIG. 7B shows detection of RT1.A$^a$ on cells transfected with WT-RT1.A$^a$.
Figure 7C:
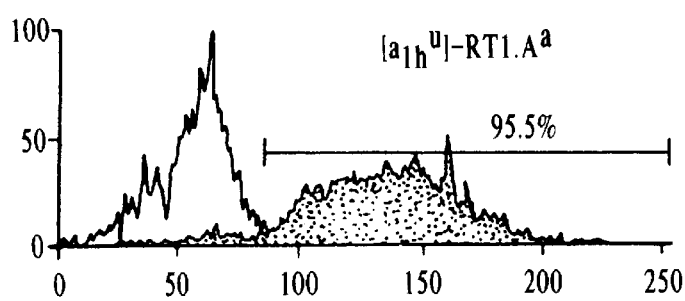
FIG. 7C shows detection of RT1.A$^a$ on cells transfected with α-1h$^u$-RT1.A$^a$.
Figure 7D:
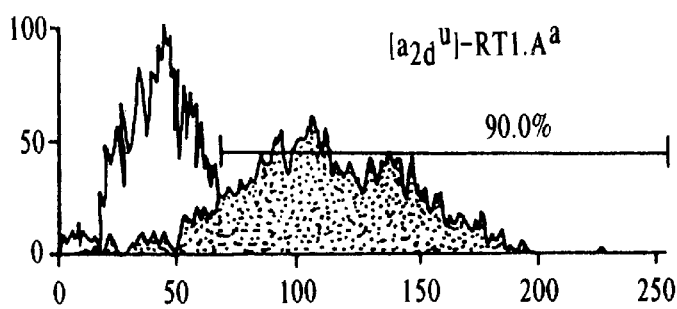
FIG. 7D shows detection of RT1.A$^a$ on cells transfected with α-1d$^u$-RT1.A$^a$.
Figure 7E:
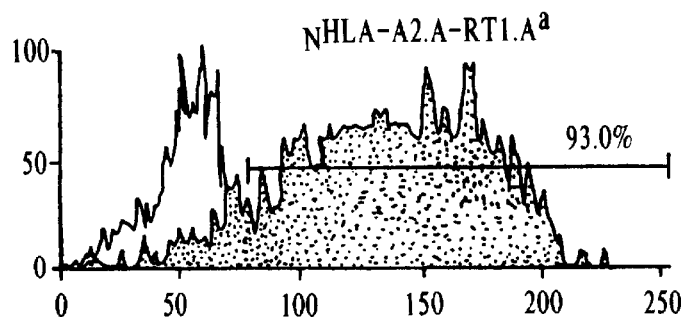
FIG. 7E shows detection of RT1.A$^a$ on cells transfected with N$^{HLA-A2.1}$-RT1.A$^a$.

The alpha-$2D^u$-$RT.1A^a$ mutant contains the entire alpha-$2^u$ domain (amino acids 91–182), thus changing $Glu^{97}$ to Arg, $Ser^{105}$ to Thr, $Glu^{148}$ to Asp, $Arg^{151}$ to Gly, $Try^{152}$ to Val, $Ser^{169}$ to Arg, $Leu^{174}$ to His, and $Ser^{182}$ to Leu. Six internal primers: F, G, H, I, J, and K were utilized in four initial PCR reactions as shown in FIG. 5C; PCR 1 (primers A and F, lane 2), PCR 2 (primers G and H, lane 3); PCR 3 (primers I and J, lane 4); and PCR 4 (primers K and L, lane 5). The four PCR fragments (400, 150, 120 and 990 base pairs) were SOEd in one final PCR reaction (primers A and L, lane 6).

Subcloning and Sequencing of PCR Products

The wild-type and mutated $RT1.A^a$ PCR products were individually ligated into the pT7Blue T-Vector (Novagen, Madison, Wis.), containing a single 3' dT residue at each end and an ampicillin resistance gene using T4 DNA ligase (Promega, Madison, Wis.). Epicurean Coli XL-1Blue MRF' competent cells (Stratagene, La Jolla, Calif.) were transformed by the ligation mixture into ampicillin-resistant cells and plated on LB ampicillin plates. Surviving colonies were separately grown in 5 ml LB medium containing ampicillin (100 mg/ml), plasmid DNA was extracted by mini-prep and digested by EcoR I to screen for the presence of the 1.6 kb $RT1.A^a$ fragment. Positive colonies were separately cultured in 250 ml of LB ampicillin medium and plasmid DNA was extracted by maxi-pre using Qiagen-tips 500 (Qiagen, Chatsworth, Calif.) according to the manufacturer's specifications. Sequencing of plasmid DNA was performed in both directions with the fluorescene-based Taq dyedeoxy™ terminator cycle sequencing kit (Applied Biosystems, Foster City, Calif.) using two outside and multiple internal primers. In brief, a 20 $\mu$l reaction (TACS buffer, dNTP mix, dyedeoxy A, G, T and C terminators, ampliTaq DNA polymerase, DNA templates and primers) was subjected to 25 thermal cycling reactions (96° C. at 30 sec.; 50° C. at 15 sec.; and 60° C. at 4 min.), purified on Centri-Sep spin columns (Princeton Separations, Adelphia, N.J.) and loaded on an Applied Biosystems 373A DNA Sequencer. Data analysis was performed by a Macintosh II Ci computer using ABI 373A analysis software (version 1.1.1). The altered amino acid and nucleic acid sequences are shown in FIG. 6, where changed residues are underlined and dots indicate no change from the wild-type $RT1.A^a$ sequences.

Transfection of BUF ($RT1^b$) hepatoma cells

Wild-type or mutated $RT1.A^a$ cDNA subcloned in the eucaryotic expression vector pSG5 (stratagene, LaJolla, Calif.) containing the SV40 promoter were utilized for transfection of the BUF Morris hepatoma 7316A cells (Masuji et al.; 1974, *Acta Med Okyama* 28: 281–293) using the lipofectin reagent (Gibco, Grand Island, N.Y.; Felinger et al., 1987). Lipofectin (25 $\mu$l)-plasmid DNA (10 $\mu$g; pSG5-$RT1.A^a$:pSV2NEO; 10:1) complexes were added to $2\times10^5$ cells in a 4 ml serum-free medium (Complete RPMI; Sigma, St. Louis, Mich.)) in 60 mm tissue culture dishes. Following a 6 hour incubation at 37° C., the medium was replaced with 10% Fetal Calf Serum (FCS)-RPMI. After 48 hours of further incubation, stable transfectants were selected by addition of 400 $\mu$g/ml (final concentration) of Geneticin (G418; Gibco, Grand Island, N.Y.). Surviving colonies were expanded and analyzed for surface expression of $TR1.A^a$.

Flow cytometry analysis was performed as described for Example 1, to detect surface expression of wild-type or chimeric $RT1.A^a$ surface expression on transfected BUF ($RT1^b$) cells.

All of the stable chimeric transfectants displayed similar levels of surface staining, i.e., greater than 90%, in contrast to their non-tranfected hepatoma counterparts, which showed only approximately 38% surface staining. These results are shown in FIGS. 7A–E, and in Table 3.

TABLE 3

| TRANSFECTANTS | SURFACE STAINING |
| --- | --- |
| Non-Transfected BUF | 38% |
| WT-$RT1.A^a$ | 91.7% |
| $\alpha$-$1^u$-$RT1.A^a$ | 95.5% |
| $\alpha$-$2d^u$-$RT1.A^a$ | 90.0% |
| $N^{HLA-A2-1}$-$RT1.A^a$ | 93.0% |

Example 3

IMMUNOGENICITY OF CHIMERIC $RT1.A^a$ ANTIGENS IN BUF HOSTS

Adult, male inbred buffalo rats (BUF; $RT1^b$) were purchased from Harlan Sprague Daroley (Indianapolis, Ind.) and housed in wire-bottomed cages with light/dark cycles. Rats were given free access to water and rat chow. The BUF hosts, which bear the same haplotype as the transfected hepatoma cell line, were injected subcutaneously with $2\times10^7$ cells bearing either wild typea or the mutated chimeric antigens of Example 2, seven days prior to transplantation with an ACI ($RT1^a$) or a Wistar Furth (WFu; $RT^a$) heart allograft.

Cardiac transplantation was carried out as described for Example 1.

As shown in Table 4, injection of cells bearing chimeric MHC Class I antigen having a substituted alpha-$2^u$ domain sequence or a substituted N-terminal HLA sequence, both immunized BUF ($RT1^b$) hosts toward grafts from ACI ($RT1^a$), but not WFu ($RT1^u$) donors. In contrast, the chimeric antigen bearing substituted alpha-$1^u$ helical sequences sensitized BUF ($RT1^b$) recipients to WFu ($RT1^u$) but not to ACI ($RT1^a$) donor alloantigens. These findings indicate that the alpha-1 helical region, but not the alpha-2 domain of $RT1.A^a$ and $RT1.A^u$ Class 1 alloantigens contains the dominant immunogenic epitopes that induce accelerated graft rejection. Further, the N-terminala epitope present in the mutant substituted with alpha-$1^u$ helical sequences failed to induce accelerated rejection of ACI ($RT1^a$) grafts.

TABLE 4

| Donor-Recipient Strains | Immunogen | Polymorphic epitopes | | | Mean Survival Days ± SD | P |
|---|---|---|---|---|---|---|
| | | α-1N | α-1h | α-2 | | |
| ACI (RT1$^a$) | — | — | — | — | 5.4 ± 0.5 | — |
| | WT-RT.1A$^a$ | a | a | a | 3.3 ± 0.5 | <0.001 |
| | N$^{HLA-A2.1}$-RT1.A$^a$ | HLA | a | a | 3.6 ± 0.5 | <0.001 |
| BUF (RT1$^b$) | α2$^u$-RT1.A$^a$ | a | a | u | 3.8 ± 0.4 | <0.001 |
| | α1$^u$-RT1.A$^a$ | a | u | a | 5.5 ± 0.5 | NS |
| WF(Rt1$^u$) | — | — | — | — | 6.0 ± 0 | — |
| | WT-RT.1A$^a$ | a | a | a | 5.6 ± 0.5 | NS |
| BUF (RT1$^b$) | N$^{HLA-A2.1}$-RT1.A$^a$ | HLA | a | a | 5.5 ± 0.6 | NS |
| | α-2$^u$-RT1.A$^a$ | a | a | u | 5.4 ± 0.5 | NS |
| | α-1$^u$-RT1.A$^a$ | a | u | a | 4.4 ± 0.5 | <0.001 |

Example 4
IMMUNOGENICITY OF CHIMERIC RT1.A$^a$ ANTIGENS IN WF RECIPIENTS

Adult male inbred WF (RT1$^u$) rats were purchased and housed as described for Example 3. WF rats bear a similar haplotype to the substituted sequences of the chimeric MHC Class 1 molecules α-1hu-RT1.A$^a$ and α-2d$^u$-RT1.A$^a$. These animals were immunized by subcutaneous injection with graded doses of 1×10$^5$–2×10$^7$ ACI (RT1$^a$) spleen cells, or with hepatoma cells transfected with the chimeric mutants WT-RT1.A$^a$, N$^{HLA-A2.1}$-RT1.A$^a$, α-1hu-RT1.A$^a$ or α-2d$^u$-RT1.A$^a$ seven days prior to transplantation with ACI (RT1$^a$) heart allografts according to the methods described for Examples 1 and 3.

Immunization with 10×10$^6$ ACI (RT1$^a$) spleen cells shortened the mean survival time of transplanted animals from 5.4±0.5 days to 2.3±0.5 days (p<0.001), while 20×10$^6$ WT-RT1.A$^a$ or N$^{HLA-A2.1}$-RT1.A$^a$ (lacking N$^a$ epitope) accelerated ACI (RT1$^a$) graft rejection to 2.8±0.4 days (p<0.001) and 4.2±0.4 days (p<0.001), respectively. These data are shown in Table 5.

Figure 8:
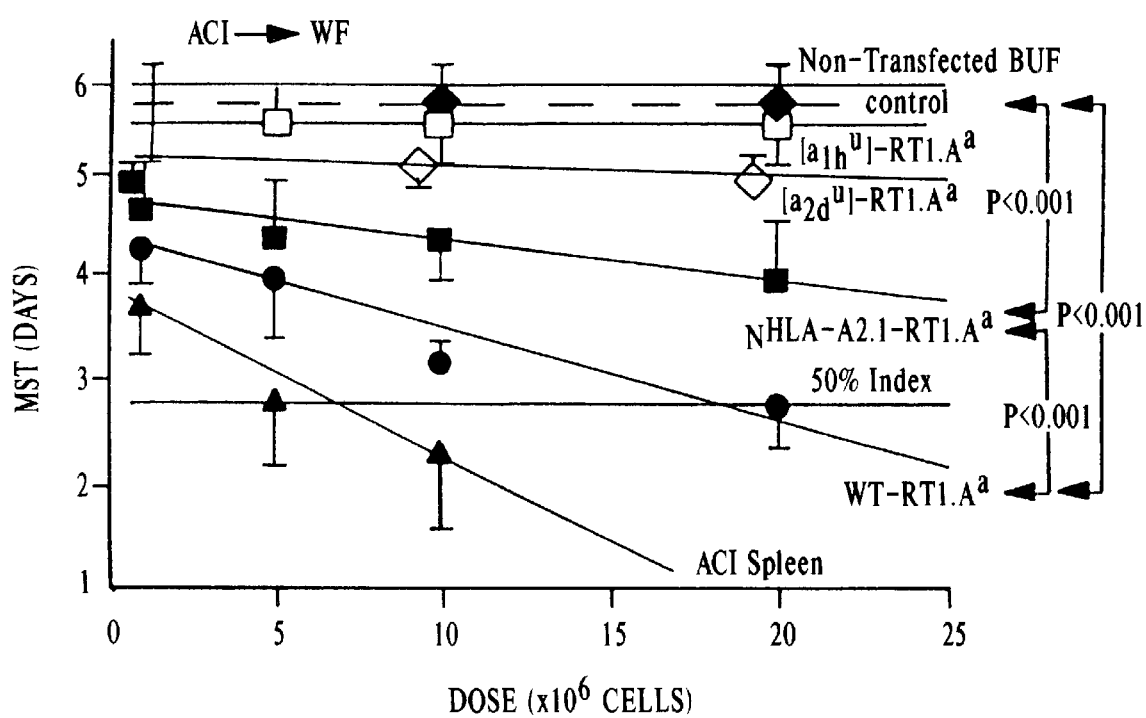
FIG. 8 is a graph showing immunogenicity of chimeric RT1.A$^a$ antigens in WF hosts, represented as dose-dependent immunization toward ACI (RT1$^a$). WF rats were injected subcutaneously with 10$^5$–2×10$^7$ cells 7 days prior to an ACI heart allograft challenge. Mean survival time was calculated in days. There were at least five rats in each group. The dashed horizontal line represents the mean survival time (5.4±0.5 days) of ACI grafts in untreated WF recipients. The solid horizontal line (50% index) represents 50% reduction of survival time. Subcutaneous injection of ACI spleen cells (filled triangles) displayed 2.6 times and 7.6 times greater immunogenicity than WT-RT1.A$^a$ (filled circles) and N$^{HLA-A2.1}$-RT1.A$^a$ (filled squares) transfectants, respectively. The chimeras α-1h$^u$-RT1.A$^a$ (open squares), α-2d$^u$-RT1.A$^a$ (open diamonds) and non-transfected hepatoma cells (filled diamonds) displayed no immunogenic ability.

In contrast, the putatively immunogenic N$^a$ and α-1h$^a$ epitopes present in the α-2d$^u$-RT.1A$^a$ chimeric transfectant failed to immunize WF recipients (mean survival time: 4.9±0.4, NS; FIG. 8), although this mutant sensitized BUF (RT1$^u$) animals against ACI (RT1$^a$) hearts (see Example 3, Table 4). Host-type α-2d$^u$ flanking sequences downregulated host responses toward immunogenic donor-type α-1$^a$ epitopes.

To confirm this downregulation, limiting dilution analysis was performed to quantitate the in vitro frequency of anti-ACI cytotoxic T cells (fTc) among the lymph node (LN) cells in normal and immune WF rats.

Limiting dilution analysis

A set of 24 replicates of each serial dilution of responder cells from 1:25,600 to 1:400 were seeded into 96-well round bottomed microtiter plates containing 5×10$^4$ irradiated (2000 rads) allogeneic splenic stimulators per well in complete RPMI 1640 medium supplemented with 10% heat inactivated FCS and 10 units/ml of purified IL-2 (Collaborative Research Inc., Bedford, Mass.), using the methods described in Ito et al., 1990, *Transplantation* 49:

TABLE 5

| Donor-Recipient Strain | Immunogen | Polymorphic epitopes | | | Mean Survival Days ± SD | P |
|---|---|---|---|---|---|---|
| | | α-1-N | α-1-h | α-2 | | |
| ACI (RT1$^a$) | — | — | — | — | 5.4 ± 0.5 | — |
| | ACI Spleen Cells | a | a | a | 2.3 ± 0.5 | <0.001 |
| | | a | a | a | 2.8 ± 0.4 | <0.001 |
| WF (RT1$^u$) | WT-RT.1A$^a$ | HLA | a | a | 4.2 ± 0.4 | <0.001 |
| | N$^{HLA-A2.1}$-RT1.A$^a$ | a | a | u | 4.9 ± 0.4 | NS |
| | α2$^u$-RT1.A$^a$ | a | u | a | 5.4 ± 0.5 | NS |
| | α1$^u$-RT1.A$^a$ | | | | | |

As shown in FIG. 8, in order to half the mean survival time (50% index), WF recipients must be injected with 7.5×10$^6$ ACI cells, 20×10$^6$ WT-RT1.A$^a$ or 57×10$^6$ N$^{HLA-A2.1}$-RT1.A$^a$ transfectants.

However, administration of 20×10$^6$ α-1hu-RT1.A$^a$ transfectants, which lack the α-1$^a$ helical epitope, failed to induce accelerated rejection of ACI (RT1$^a$) grafts (mean survival time: 5.4±0.5, NS; FIG. 8). This data confirms the presence of an immunodominant immunogenic epitope in this region. The immunogenic difference between WT-RT1.A$^a$ and N$^{HLA-A2.1}$-RT1.A$^a$ transfectants (p<0.001; FIG. 8) suggests that substitution of the N-terminus eliminates a subdominant immunogenic epitope.

422–428. After 7 days of incubation at 37° C., the cytotoxic activity of each well was assessed during an additional 6 hour incubation at 37° C. with 1×10$^4$ ACI or WF target cells previously stimulated with Concanavalin A (Con A) (3-day) and labeled with specific activity 200–500 mCi/mg Cr; Amersham, Arlington, Ill.). Release of $^{51}$Cr from supernates harvested using a cartridge collection system (Skatron Inc., Sterling, Va.) was measured in a gamma counter.

Positive results were defined as values exceeding the mean spontaneous chromium release by more than 3 standard deviations (SD). Minimum chi-square estimates with 95% confidence limit of the fTc were obtained by the Poisson distribution relationship between responder-cell number and the natural logarithm of the fraction of negative cells. A divergence less than 10% between the maximum likelihood estimate and the minimum chi-square value with a probability greater than 0.05 as estimated from a chi-square table was regarded as consistent with "a single hit" Poisson model.

Figure 9:
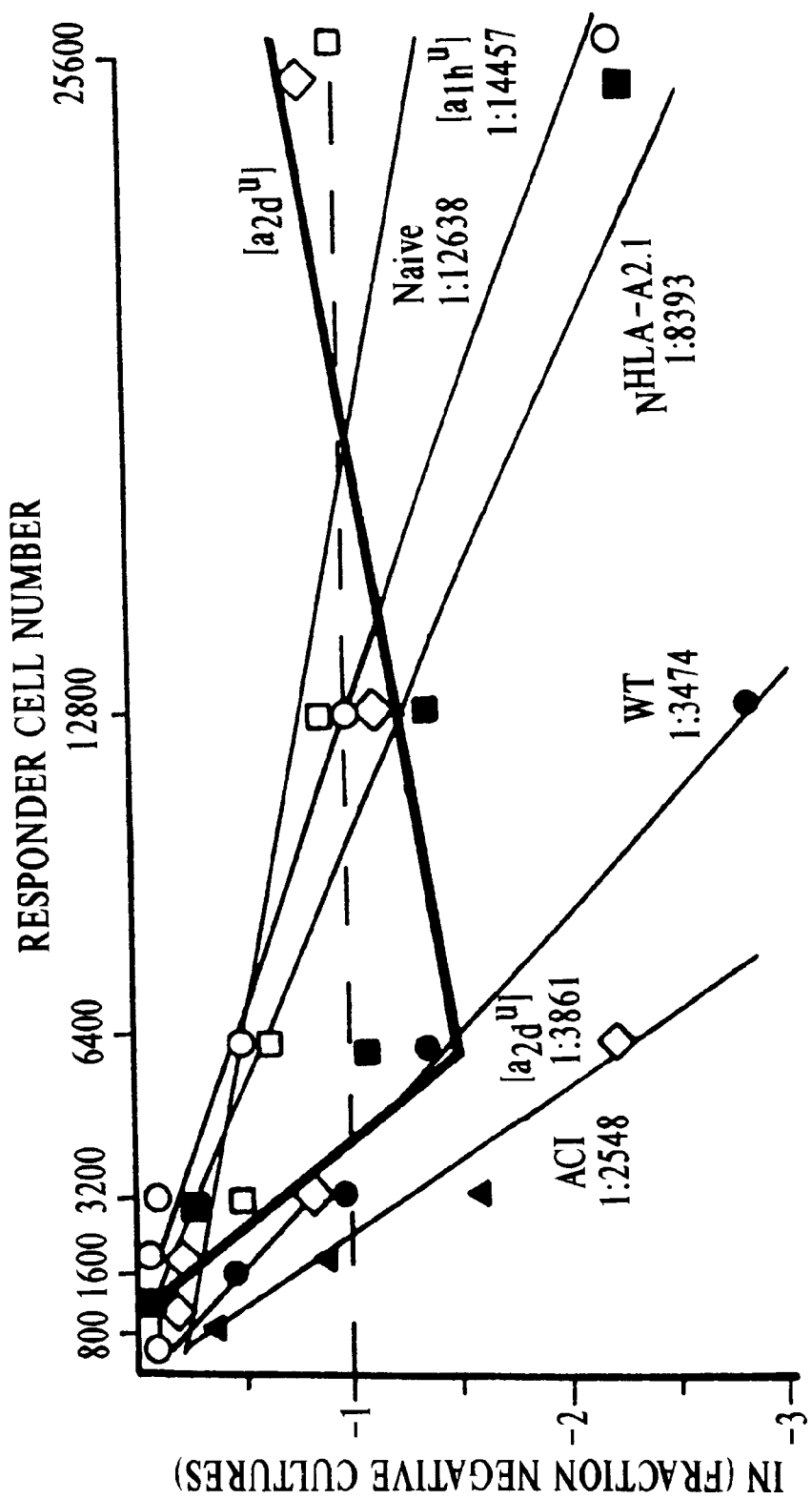
FIG. 9 is a graph showing the frequency of anti-ACI (RT1$^a$) cytotoxic T cells in lymph node cells obtained from WF rats 7 days following administration of 2×10$^7$ ACI spleen cells (filled triangles), WT-RT1.A$^a$ (filled circles), N$^{HLA-A2.1}$-RT1.A$^a$ (filled squares), α-1h$^u$-RT1.A$^a$ (open squares), α-2d$^u$-RT1.A$^a$ (open diamonds) transfectants, non-transfected hepatoma cells (filled diamonds), and naive, non-treated hosts (open circles). Data was generated by limiting dilution analysis.

The data are shown in FIG. 9. As expected, the administration of ACI spleen cells or WT-RT1.A$^a$ transfectants, both of which induce accelerated graft rejection, increased the fTc from 1:12638 in naive animals to 1:2548 and 1:3474, respectively. In contrast, α-2d$^u$-RT.1A$^a$ transfectants, which did not accelerate allograft rejection initially increased fTc to 1:3861, and then exhibited a V-shaped profile characteristic of negative regulatory cells whose activity is evident at fTc values less than 1:64000 (Florence et al., 1989, *Transplantation* 47:156, 162).

Alloantibody detection

Figure 10A:
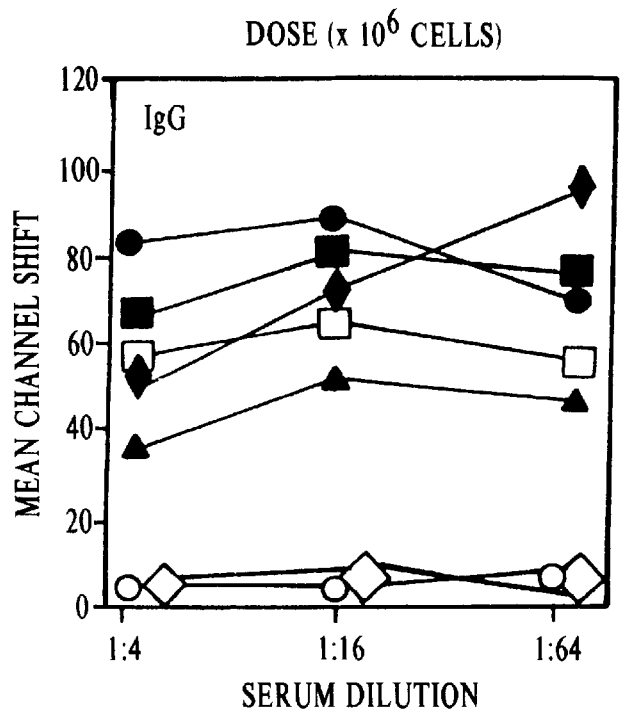
FIGS. 10A–C are graphs showing anti-RT1$^a$ alloantibody production in WF rats treated with ACI spleen cells or chimeric RT1.A$^a$ transfectants: ACI spleen cells (filled triangles), WT-RT1.A$^a$ (filled circles), N$^{HLA-A2.1}$-RT1.A$^a$ (filled squares), α-1h$^u$-RT1.A$^a$ (open squares), and a-2d$^u$-RT1.A$^a$ (open diamonds) transfectants. Control sera was obtained from naive, non-treated hosts (open circles) or from WF rejectors of ACI hearts (filled diamonds).
Figure 10B:
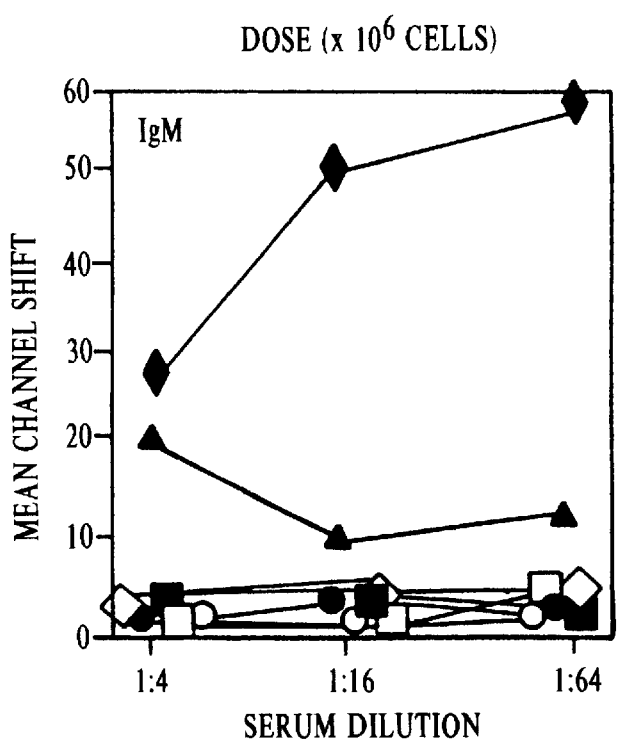

Anti-ACI (RT1$^a$) binding alloantibodies were detected in the sera obtained from treated WF rats one week following treatment by incubation at 4° C. for 30 minutes of serially diluted experimental sera (1:4, 1:16 or 1:64) with ACI lymph nodes (3×10$^3$). After washing, 50 μl of FITC-conjugated rabbit anti-rat IgG (1:250) or rabbit anti-rat IgM (1:100) were added for a second incubation. Cells were washed and fixed. The intensity of staining was expressed as mean channel shift (MCS), namely the difference between the sample's mean fluorescence and the mean fluorenscence obtained by the second fluoresceinated antibody only. Binding to anti-IgG is shown in FIG. 10A, and to anti-IgM in FIG. 10B.

Cytotoxic anti-ACI alloantibodies in experimental sera was detected by a two-stage complement-dependent antibody-mediated cytotoxicity assay. Sera were heat-inactivated at 56° C. for 30 minutes and serially diluted in a 96-well microtiter plate using HBSS with 5% FCS. $^{51}$Cr-labeled ACI lymph node target cells (1×10$^5$) were added to each well and incubated at 4° C. for 30 minutes. Cells were washed prior to the addition of 50 ml (1:8 dilution) of "low toxicity" rabbit complement (Cedar Lane, Toronto, Canada), followed by a 30-minute incubation at 37° C. Supernates were collected and radioactivity determined in a Beckman gamma counter. Maximum lysis was based on $^{51}$Cr release from labeled targets upon treatment with 0.8% Triton (Sigma, St. Louis, Mo.). The background count obtained by incubation with complement alone was less than 10% maximum lysis. The percent specific lysis was determined as:

$$\% \text{ specific lysis} = \left( \frac{\text{experimental} - \text{complement background}}{\text{maximum} - \text{complement background}} \right) \times 100$$

Figure 10C:
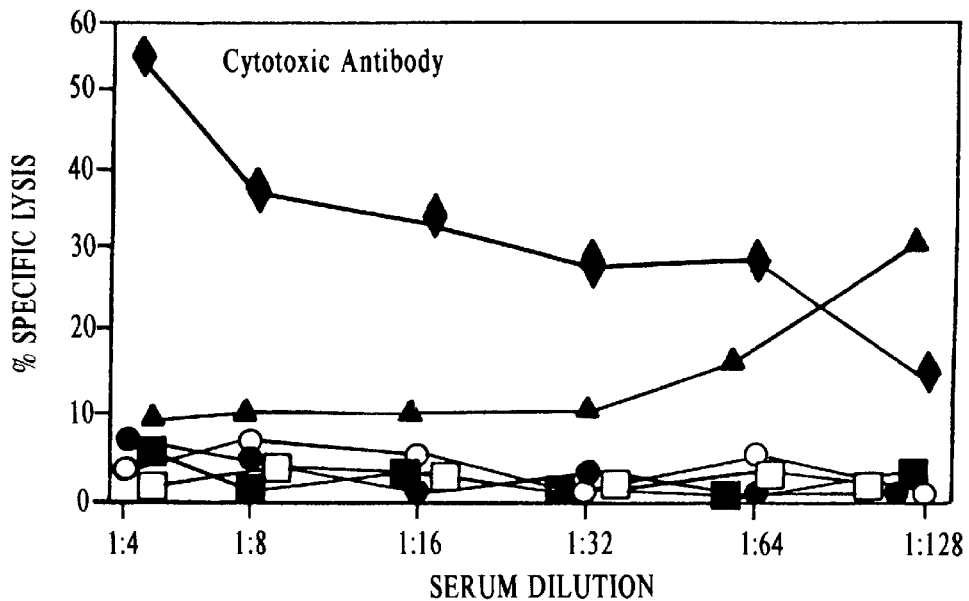

The presence of cytotoxic antibody is shown in FIG. 10C.

The injection of α-2d$^u$-RT.1A$^a$ transfectants into WF (RT1$^u$) hosts failed to stimulate the production anti-RT1$^a$ alloantibodies. In contrast, transfectants bearing WT-RT1.A$^a$, N$^{HLAA\text{-}A2.1}$-RT1.A$^a$, and α-1hu-RT1.A$^a$ all evoked the production of non-complement-dependent IgG, but not IgM, antibodies. These results demonstrated that the combination of donor-type α-1$^a$ immunogenic domain with recipient-type α-2$^u$ domain induces a potent regulatory response that inhibits sensitization toward allografts.

Example 5
IMMUNOGENICITY OF CHIMERIC RT1.A$^a$ ANTIGENS IN ACI RECIPIENTS

Figure 11:
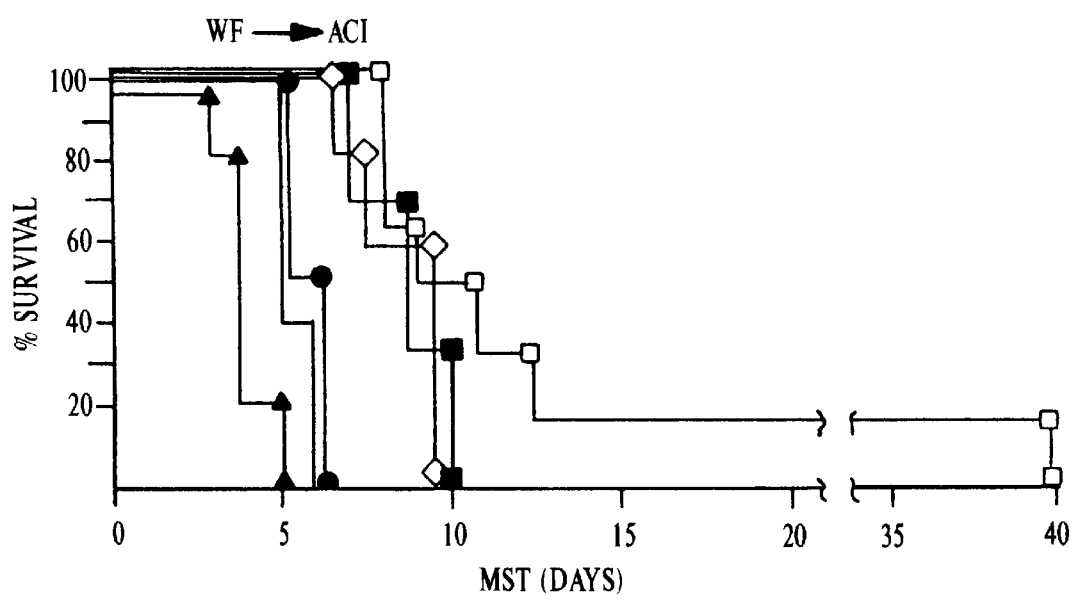
FIG. 11 is a graph showing the effect of subcutaneous administration of chimeric RT1.A$^a$ antigens in ACI hosts on in vivo immunization of ACI (RT1$^a$) recipients of WF (RT1$^u$) heart allografts. ACI rats were untreated (broken lines) or immunized with WT-RT1.A$^a$ (filled circles), N$^{HLA-A2.1}$-RT1.A$^a$ (filled squares), α-1h$^u$-RT1.A$^a$ (open squares), α-2d$^u$-RT1.A$^a$ (open diamonds) transfectants or WF spleen cells (filled diamonds) seven days prior to WF (RT1$^u$) heart allograft challenge.

WF (RT1$^u$) spleen cells, wild type, or chimeric-RT1.A$^a$ transfectants (2×10$^7$) were injected subcutaneously into ACI (RT1$^a$) recipients, which bear a similar haplotype to the backbone of the chimeric antigens of Example 2, seven days prior to grafting WF (RT1$^u$) hearts, using the methods and analysis described in the preceding examples. The mean survival times of the treated animals are shown in Table 6 and FIG. 11.

TABLE 6

| IMMUNOGEN | MEAN SURVIVAL TIME DAYS ± SD | P |
|---|---|---|
| — | 5.4 ± 0.6 | — |
| WF spleen cells | 4.0 ± 0.7 | <0.01 |
| WT-RT1.A$^a$ | 5.5 ± 0.5 | NS |
| N$^{HLA\text{-}A2.1}$-RT1.A$^a$ | 8.7 ± 1.0 | <0.01 |
| α-2d$^u$-RT1.A$^a$ | 9.2 ± 1.3 | <0.001 |
| α1h$^u$-RT1.A$^a$ | 14.0 ± 10.3 | <0.01 |

WF spleen cells shortened the mean survival time of transplant recipients from 5.4±0.6 days to 4.0±0.7 days (p<0.01), while the syngeneic WT-RT1.A$^a$ transfectants were not effective (5.5±0.5; NS). N$^{HLA\text{-}A2.1}$-RT1.A$^a$, α-2d$^u$-RT.1A$^a$ and α-1h$^u$-RT1.A$^a$ transfectants all modestly prolonged the mean survival time of transplanted WF (RT1$^u$) hearts from 5.9±0.6 days in untreated controls to 8.7±1.0 days (p<0.01), 9.2±1.3 days (p<0.001) and 14.0±10.3 days, respectively (p<0.01).

Figure 12:
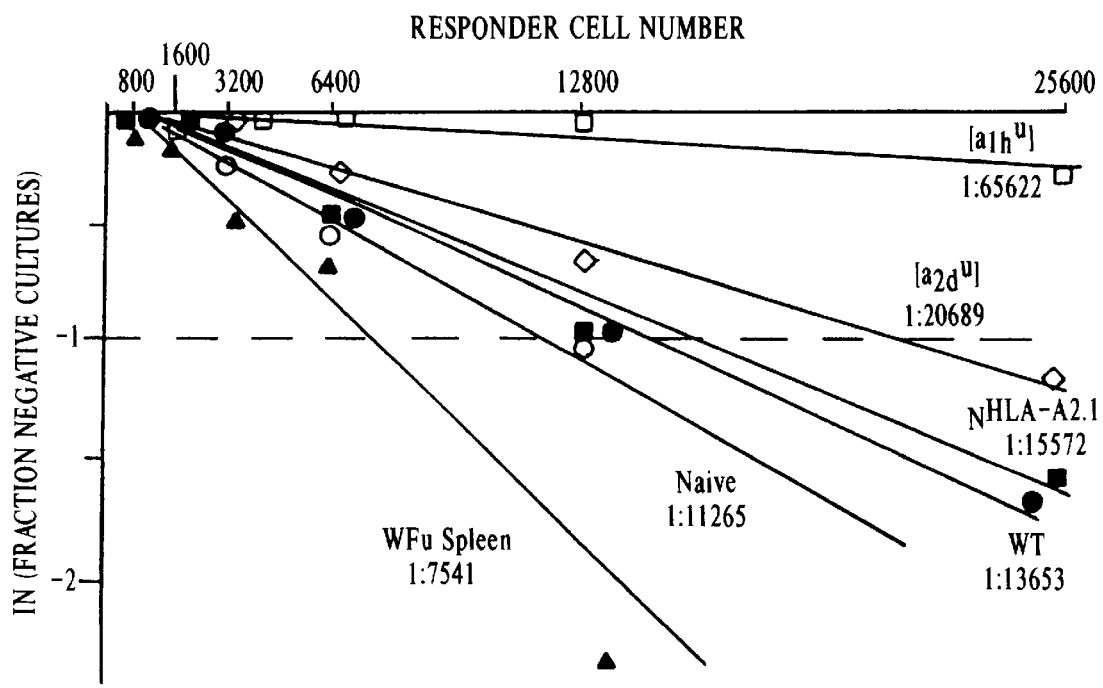
FIG. 12 is a graph showing the frequency of anti-WF (RT1$^u$) cytotoxic T cells in lymph nodes obtained from ACI rats following treatment with WT-RT1.A$^a$ (filled circles), N$^{HLA-A2.1}$-RT1.A$^a$ (filled squares), α-1h$^u$-RT1.A$^a$ (open squares), α-2d$^u$-RT1.A$^a$ (open diamonds) transfectants, WF spleen cells (filled diamonds), or non-treated naive hosts (open circles). Data were obtained by limiting dilution analysis.

Furthermore, as shown in Table 7 and FIG. 12, immunization with transfectants bearing N$^{HLA\text{-}A2.1}$-RT1.A$^a$, α-2d$^u$-RT.1A$^a$ or α-1h$^u$-RT1.A$^a$ reduced the fTc toward WF alloantigens among lymph node cells of ACI (RT1$^a$) rats, from 1:11264 in naive animals to 1:15572, 1:20689 and 1:65622, respectively. In contrast, immunization with WF spleen cells increased the fTc to 1:7541. These findings demonstrate the potential tolerogenicity of chimeric RT1.A$^a$ molecules, particularly those bearing donor α-1 helix flanked by recipient N-terminal and α-2 domain sequences, even upon immunogenic subcutaneous delivery.

TABLE 7

| IMMUNOGEN | FREQUENCY OF ANTI-WF Tc CELLS |
|---|---|
| Naive control | 1:11265 |
| WF spleen cells | 1:7541 |
| WT-RT1.A$^a$ | 1:13653 |
| N$^{HLA\text{-}A2.1}$-RT1.A$^a$ | 1:15572 |
| α-2d$^u$-RT1.A$^a$ | 1:20689 |
| α-1h$^u$-RT1.A$^a$ | 1:65622 |

Example 6
INDUCTION OF TOLERANCE BY α-1$^u$-RT1.A$^a$ TO RT1$^u$ ALLOGRAFTS IN RT1$^a$ RECIPIENTS The tolerogenicity of quasi-self chimeric antigens was further examined in the clinically relevant model of peri-transplant administration of antigen in combination with CsA therapy. This model is described, for example in Didlake et al, 1988 *Transplantation* 46:743–747; Florence et al., 1989 *Transplantation* 47:156–162; Ito et al., 1990 *Transplantation* 49:422–428; Hamashima et al., 1994, in press; Yasumura et al., 1983 *Transplantation* 36:603–609.

In addition to a seven day oral CsA course (10 mg/kg; day 0–6), ACI (RT1$^a$) recipients of WF (RT1$^u$) hearts received a single immediately pre-operative, portal venous injection of 3M KCl extract (10 mg) prepared from N$^{HLA\text{-}A2.1}$-RT1.A$^a$, α-1h$^u$-RT1.A$^a$ or α-2d$^u$-RT.1A$^a$ transfectants, from non-transfected BUF hepatoma cells (RT1$^b$), or from donor-type WF (RT1$^u$) hepatocytes.

The KCl-extracts were prepared from cells by treatment for 18 hours with 3m KCl followed by configuration, concentration of protein and dialysis with PBS as described in Reisfeld and Kahan, 1970, *Fed. Proc.* 29:2034–2040.

Figure 13:
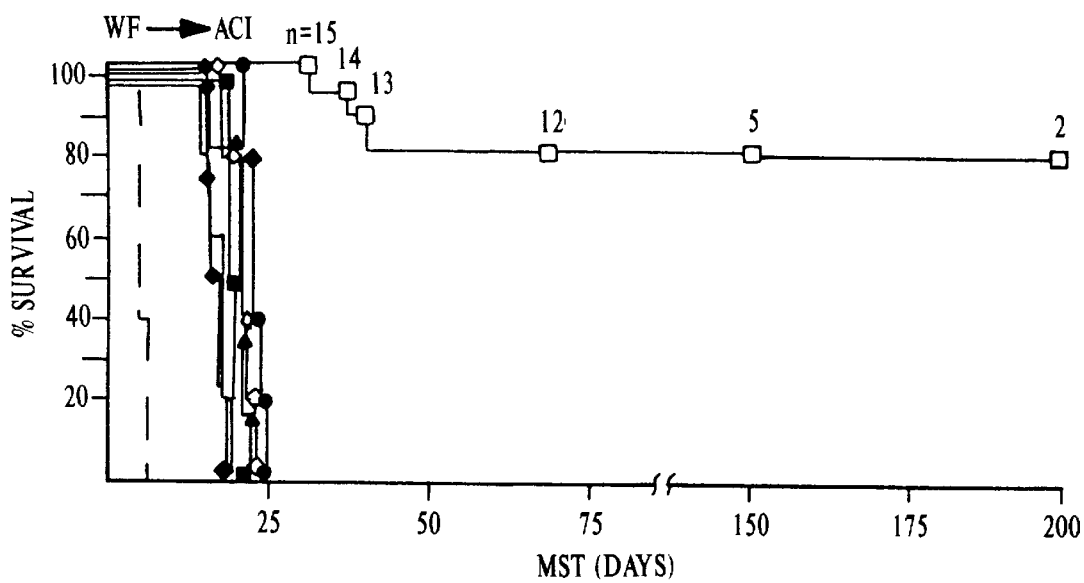
FIG. 13 is a graph showing tolerance induction by peri-transplant administration of e-HAg-chimeras combined with cyclosporine. ACI (RT1$^a$) recipients of WF (RT1$^u$) hearts were untreated (broken lines) or treated with a 7 day course of oral CsA alone (solid lines) or in combination with a single injection of e-HAg obtained from WT-RT1.A$^a$ (filled circles), N$^{HLA-A2.1}$-RT1.A$^a$ (filled squares), α-1h$^u$-RT1.A$^a$ (open squares), α-2d$^u$-RT1.A$^a$ (open diamonds) transfectants, WF liver cells (filled arrowheads), or non-transfected BUF hepatoma cells (filled diamonds)

MHC antigen (e-HAg) was extracted with 3M KCl from normal BUF hepatoma cells, WT or from stable chimeric transfectants, as previously described (Reisfeld and Kahan, 1970, *Fed. Proc.* 29:2034–2040). The MHC antigen, e-HAg (10 mg) was administered via the portal vein on the day of transplantation immediately followed by 7 daily doses of 10 mg/kg/day of CsA delivered by oral gavage from day 0 to 6. CsA powder was obtained form Sandoz (Basel, Switzerland) and dissolved in a mixture of 1% ethyl alcohol and 99% Cremophor (Sigma, St. Louis, Mo.). The data are shown in Table 8 and FIG. 13.

TABLE 8

| e-HAg Antigen | CsA | Mean ± SD Survival (Days) | P |
|---|---|---|---|
| — | − | 5.4 ± 0.6 | — |
| — | + | 16.2 ± 1.6 | — |
| Wfu liver (RT1$^u$) | + | 20.4 ± 1.1 | |
| BUF Hepatoma (RT1$^b$) | + | 16.5 ± 1.2 | |
| WT-RT1.A$^a$ | + | 21.6 ± 1.2 | |
| N$^{HLA\text{-}A2.1}$-RT1.A$^a$ | + | 17.8 ± 0.8 | |
| α-2d$^u$-RT1.A$^a$ | + | 19.2 ± 2.2 | |
| α-1h$^u$-RT1.A$^a$ | + | >170 | <0.001 |

Administration of CsA alone prolonged WF heart allograft survival to 16.2±1.6 days. There was no additional effect of KCl extracts from WF (RT1$^u$) hepatocytes, WT-RT1.A$^a$, N$^{HLA\text{-}A2.1}$-RT1.A$^a$, α-2d$^u$-RT.1A$^a$ transfectants or non-transfected BUF hepatoma cells (FIG. 10). In contrast, α-1hu-RT1.A$^a$ extracts induced indefinite survival in 80 percent of recipients (mean survival time>170 days, p<0.001).

Among the ACI (RT1$^a$) recipients bearing WF (RT1$^u$) heart allografts for more than 60 days, five accepted donor-type WF (RT1$^u$) secondary heterotropic heart grafts (mean survival time>120 days), while three promptly rejected third-party Brown Norway (RT1$^n$) secondary heterotopic heart transplants (mean survival time 7.0±1.7). The secondary transplants were anastomosed to neck vessels.

Subsequently, these tolerant ACI recipients accepted donor-type WF skin allographs for more than 21 days (n=8) but rejected third-party Brown Norway skin allografts within 8.01±0.0 days.

These results showed that flanking α-1 immunogenic epitopes with syngeneic sequences in addition to CsA induces donor-specific transplantation tolerance.

Having described the invention above, various modifications of the techniques, procedures, material and equipment will be apparent to those in the art. It is intended that all such variations within the scope and spirit of the appended claims be embraced thereby.

We claim:

1. An allogenic chimeric major bistocompatibility complex Class I molecule comprising:
   an alpha-1 domain which alpha-1 domain includes an N-tenninal region having a first beta strand loop, and a helical region containing an immunodominant epitope; and
   an alpha-2 domain;
   wherein the immunodominant epitope in the helical region of the alpha-1 domain has been substituted with a corresponding immunodominant epitope of the helical region of an alpha-1 domain of a different allelic major histocompatibility Class I molecule.

2. The chimeric molecule of claim 1, wherein the substituted helical region is matched to a specified donor's allelic type major histocompatibility complex Class I molecule.

3. The chimeric molecule of claim 1, wherein said first beta strand loop of said N-terminal region and alpha-2 domain are matched to a specified recipient's allelic type major histocompatibility complex Class I molecule.

4. An allogenic chimeric major histocompatibility complex Class I molecule comprising:
   an alpha-1 domain, which alpha-1 domain includes an N-terminal region having a first beta strand loop, and a helical region containing an immunodominant epitope, which alpha-1 domain includes a specified recipient's allelic type first beta strand loop of said N-terminal region and a specified donor's allelic type immunodominant epitope of said helical region; and
   an alpha-2 domain of the specified recipient's allelic type, wherein the specified recipient and donor types are different allelic types of major histocompatibility Class I molecules.

5. A pharmaceutical composition for inducing recipient allograft tolerance to a donor graft, said composition comprising in a pharmaceutically acceptable carrier, and an effective tolerance-inducing amount of the allogenic chimeric major histocompatibility complex Class I molecule of claim 1.

6. The pharmaceutical composition of claim 5, wherein said chimeric molecule is provided as an extract of cells expressing the molecule.

7. The pharmaceutical composition of claim 5, wherein said chimeric molecule is provided as whole cells expressing the molecule.

8. The pharmaceutical composition of claim 5, wherein said chimeric molecule is provided as purified glycoprotein.

9. A method for inducing recipient allograft tolerance to a donor graft, comprising the step of administering to a recipient an effective tolerance-inducing amount of the allogenic chimeric major histocompatibility complex Class I molecule of claim 1.

10. The method of claim 9, wherein said administering is at the time of donor graft transplantation.

11. The method of claim 9 further comprising administration of cyclosporin.

12. The method of claim 11 wherein said cyclosporin is administered daily for approximately seven days post-transplantation.

13. The method of claim 12 wherein said administration is of a single peri-operative dose of the chimeric molecule.

14. The method of claim 9, wherein said chimeric molecule is in the form of a cellular extract.

15. The method of claim 9, wherein said chimeric molecule is in the form of cells expressing the molecule.

16. The method of claim 9, wherein said chimeric molecule is in the form of substantially purified glycoprotein.

17. The method of claim 9, wherein said administration is by injection.

18. The method of claim 17, wherein said injection is into the portal vein.

19. The method of claim 9, wherein said administration inhibits production of anti-donor antibodies in the recipient.

* * * * *